United States Patent
Hirose

(10) Patent No.: US 11,648,082 B2
(45) Date of Patent: May 16, 2023

(54) MEDICAL HOLDING DEVICE, AND MEDICAL OBSERVATION DEVICE

(71) Applicant: Sony Olympus Medical Solutions Inc., Tokyo (JP)

(72) Inventor: Kenji Hirose, Tokyo (JP)

(73) Assignee: SONY OLYMPUS MEDICAL SOLUTIONS INC., Tokyo (JP)

(*) Notice: Subject to any disclaimer, the term of this patent is extended or adjusted under 35 U.S.C. 154(b) by 909 days.

(21) Appl. No.: 16/575,394

(22) Filed: Sep. 19, 2019

(65) Prior Publication Data

US 2020/0093564 A1    Mar. 26, 2020

(30) Foreign Application Priority Data

Sep. 26, 2018  (JP) .............................. JP2018-179644

(51) Int. Cl.
 *A61B 90/50* (2016.01)
 *A61B 34/20* (2016.01)
 *A61B 90/00* (2016.01)

(52) U.S. Cl.
 CPC .............. *A61B 90/50* (2016.02); *A61B 34/20* (2016.02); *A61B 90/361* (2016.02); *A61B 2034/2059* (2016.02); *A61B 2090/066* (2016.02); *A61B 2090/067* (2016.02); *A61B 2090/504* (2016.02)

(58) Field of Classification Search
 CPC ....... A61B 90/50; A61B 34/20; A61B 90/361; A61B 2034/2059; A61B 2090/066; A61B 2090/067; A61B 2090/504
 See application file for complete search history.

(56) References Cited

U.S. PATENT DOCUMENTS

| | | | | |
|---|---|---|---|---|
| 2010/0185211 A1* | 7/2010 | Herman | ................. | A61B 90/50 606/130 |
| 2012/0150192 A1* | 6/2012 | Dachs, II | ............... | A61B 34/30 606/130 |
| 2014/0276953 A1* | 9/2014 | Swarup | .................. | A61B 50/13 606/130 |
| 2015/0250547 A1* | 9/2015 | Fukushima | .......... | A61B 90/361 606/130 |
| 2017/0080574 A1* | 3/2017 | Kuroda | .................. | A61B 34/35 |
| 2017/0086928 A1* | 3/2017 | Auld | ...................... | A61B 90/50 |
| 2019/0075230 A1* | 3/2019 | Takeda | ............. | A61B 1/000095 |

FOREIGN PATENT DOCUMENTS

| | | |
|---|---|---|
| JP | 2001054889 A | 2/2001 |
| JP | 2001-300871 A | 10/2001 |
| JP | 2010110878 A | 5/2010 |
| JP | 2017512553 A | 5/2017 |
| WO | WO-2017169650 A | 10/2017 |

\* cited by examiner

*Primary Examiner* — Zade Coley
*Assistant Examiner* — Diana Jones
(74) *Attorney, Agent, or Firm* — Xsensus LLP

(57) ABSTRACT

A medical holding device includes: an arm configured by coupling a plurality of links to each other by joints, the arm having at least seven or more degrees of freedom by rotational operations on rotation axes, and being configured to support a medical instrument; and an arm controller configured to control an operation of the arm. The arm has six degrees of freedom realized by rotational operations of six passive rotation axes that passively rotate and one or more degrees of freedom realized by rotational operations of one or more active rotation axes that actively rotate, and the arm controller is configured to rotate the active rotation axis so as to avoid a predetermined state of a posture of the arm.

20 Claims, 9 Drawing Sheets

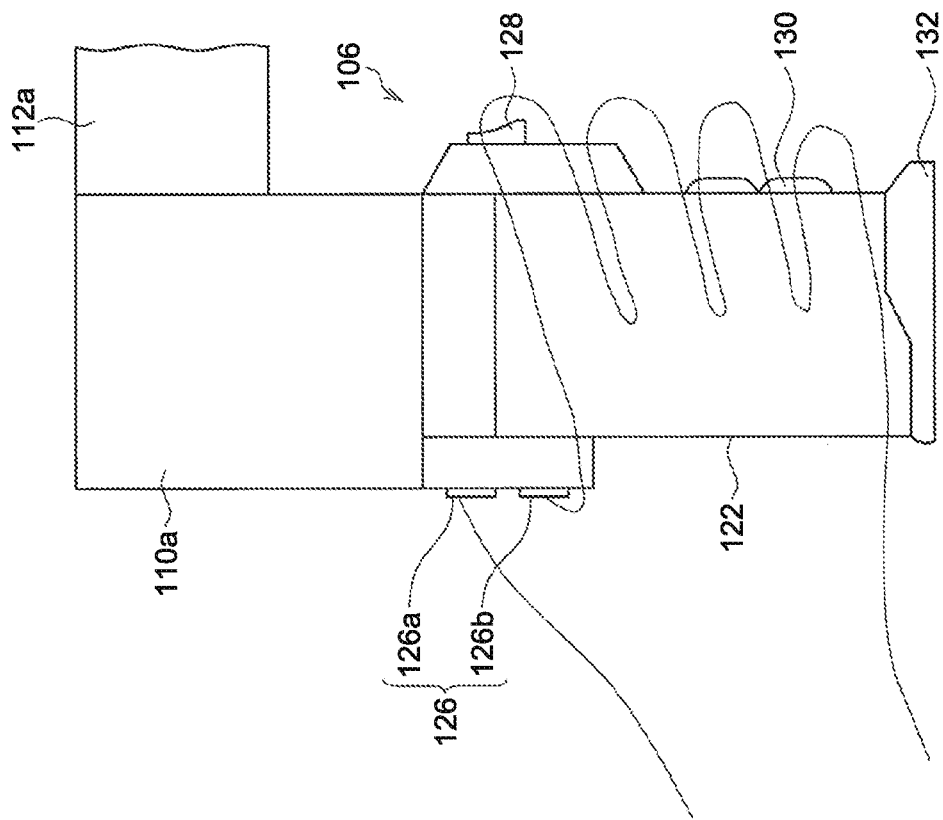
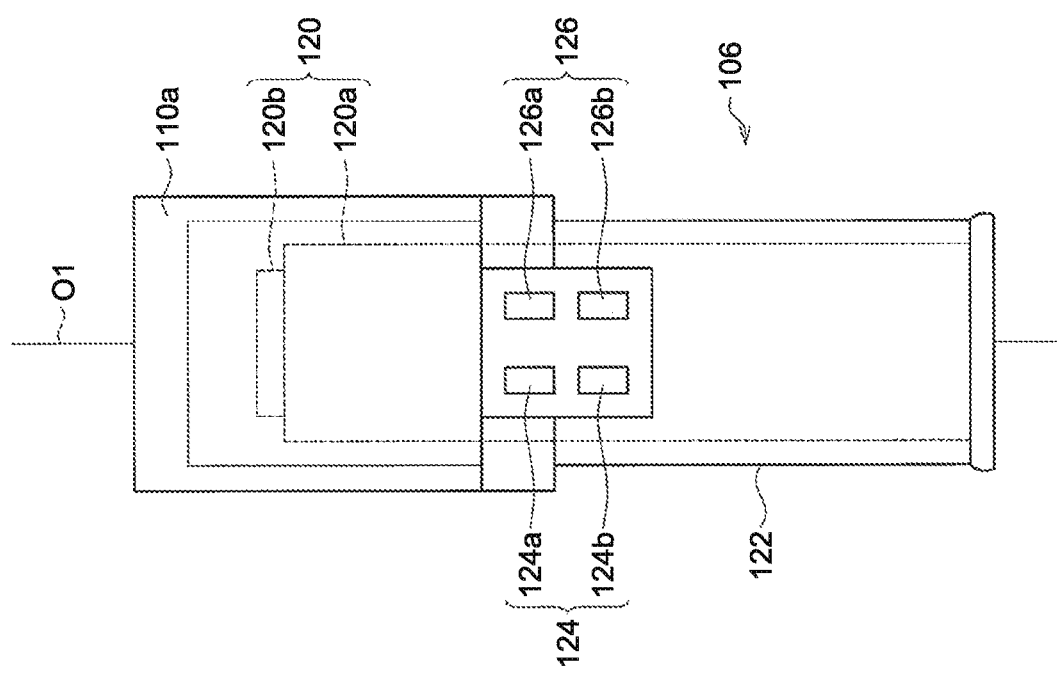

MEDICAL HOLDING DEVICE, AND MEDICAL OBSERVATION DEVICE

CROSS-REFERENCE TO RELATED APPLICATION

The present application claims priority to and incorporates by reference the entire contents of Japanese Patent Application No. 2018-179644 filed in Japan on Sep. 26, 2018.

BACKGROUND

The present disclosure relates to a medical holding device and a medical observation device.

In the medical field, recently, a medical observation device capable of magnifying and observing an observation target such as an affected site is sometimes used in order to, for example, to support microsurgery such as neurosurgery or to perform endoscopic surgery. Examples of the medical observation device include a medical observation device provided with an optical microscope and a medical observation device provided with an imaging device that functions as an electronic imaging microscope. Hereinafter, the medical observation device provided with the optical microscope will be referred to as an "optical medical observation device". In addition, the medical observation device provided with the above-described imaging device will be sometimes referred as an "electronic-imaging-type medical observation device" or simply a "medical observation device" hereinafter. In addition, an imaging image (moving image or still image, which will be similarly applied hereinafter) in which an image of an observation target has been captured by the imaging device provided in the medical observation device will be referred to as a "medical imaging image".

In the electronic-imaging-type medical observation device, improvement in image quality of an imaging device has progressed, and a high definition of a display device on which a captured image is displayed has also progressed. As a result, it is possible to display a medical imaging image, which has the same image quality as that of the observation by the optical medical observation device, on a display screen of the display device. In addition, a user who uses the electronic-imaging-type medical observation device (for example, a medical worker such as an operator and an assistant of the operator, which will be similarly applied hereinafter) does not need to look into an eyepiece constituting the optical microscope as in the case of using the optical medical observation device, and thus, can more freely move a position of the imaging device. Thus, there is an advantage that microsurgery or the like can be supported more flexibly by using the electronic-imaging-type medical observation device so that the electronic-imaging-type medical observation device has been progressively utilized in the medical field.

Meanwhile, techniques relating to control of a manipulator having a plurality of axes have been developed. As a technique relating to control of a 7-axis manipulator, a technique described in JP 2001-300871 A can be exemplified.

SUMMARY

Since the user of the electronic-imaging-type medical observation device can freely move the position of the imaging device as described above, the user can change an imaging range by moving the position of the imaging device. However, the degree of freedom of an arm is reduced depending on a posture of the arm supporting the imaging device, and thus, a "situation where it is difficult for the user to move the imaging device to capture a desired imaging range without manually changing the posture of the arm" is likely to occur. In addition, when the above situation occurs, the convenience of the user using the medical observation device is likely to deteriorate.

In addition, similarly, a "situation where it is difficult to move a medical instrument" is likely to occur even in existing medical holding devices each having an arm that supports an arbitrary medical instrument, for example, an endoscope holder, an endoscope, or the like, and the convenience of the user using the medical holding device is likely to deteriorate. Here, when the medical instrument supported by the arm of the medical holding device is the imaging device, the medical holding device functions as the medical observation device.

There is a need for a medical holding device and a medical observation device which are capable of improving convenience of a user.

According to one aspect of the present disclosure, there is provided a medical holding device including: an arm configured by coupling a plurality of links to each other by joints, the arm having at least seven or more degrees of freedom by rotational operations on rotation axes, and being configured to support a medical instrument; and an arm controller configured to control an operation of the arm, wherein the arm has six degrees of freedom realized by rotational operations of six passive rotation axes that passively rotate and one or more degrees of freedom realized by rotational operations of one or more active rotation axes that actively rotate, and the arm controller is configured to rotate the active rotation axis so as to avoid a predetermined state of a posture of the arm.

According to another aspect of the present disclosure, there is provided a medical observation device including: an imager configured to capture an image of an observation target; an arm configured by coupling a plurality of links to each other by joints, the arm having at least seven or more degrees of freedom by rotational operations on rotation axes, and being configure to support the imager; and an arm controller configured to control an operation of the arm, wherein the arm has six degrees of freedom realized by rotational operations of six passive rotation axes that passively rotate and one or more degrees of freedom realized by rotational operations of one or more active rotation axes that actively rotate, and the arm controller is configured to rotate the active rotation axis so as to avoid a predetermined state of a posture of the arm.

BRIEF DESCRIPTION OF THE DRAWINGS

FIGS. 2A and 2B are explanatory views for describing an example of a configuration of an imaging device provided in a medical observation device according to the first embodiment;

DETAILED DESCRIPTION

Figure 1:
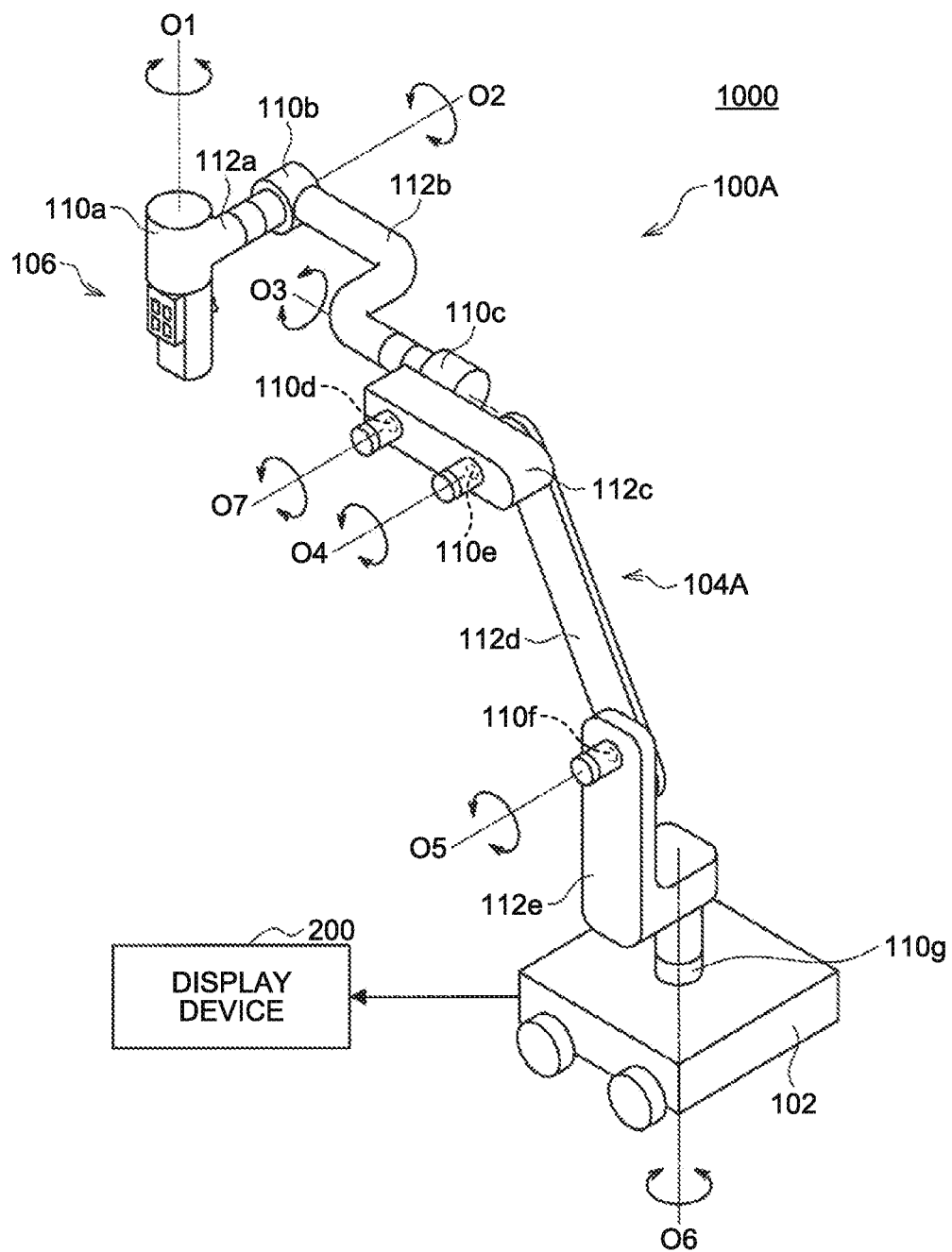
FIG. 1 is an explanatory view illustrating an example of a configuration of a medical observation system according to a first embodiment.

Hereinafter, preferred embodiments of the present disclosure will be described in detail with reference to the accompanying drawings. Incidentally, in the present specification and the drawings, components having substantially the same functional configurations will be denoted by the same reference signs, and redundant descriptions thereof will be omitted.

In addition, a description will be given in the following order hereinafter.

1. Medical Observation System According to Present Embodiment, and Control Method According to Present Embodiment

[1] Medical Observation System According to First Embodiment

[1-1] Display Device

[1-2] Medical Observation Device

[2] Control Method According to Present Embodiment

[2-1] Outline of Control Method According to Present Embodiment

[2-2] Processing Relating to Control Method According to Present Embodiment

[2-3] Example of Effect Exhibited by Medical Observation Device According to First Embodiment When Control Method According to Present Embodiment Is Applied

[3] Medical Observation System According to Second Embodiment

[3-1] Configuration of Medical Observation System According to Second Embodiment

[3-2] Example of Effect Exhibited by Medical Observation Device According to Second Embodiment When Control Method According to Present Embodiment Is Applied

[4] Medical Observation System According to Third Embodiment

[4-1] Configuration of Medical Observation System According to Third Embodiment

[4-2] Example of Effect Exhibited by Medical Observation Device According to Third Embodiment When Control Method According to Present Embodiment Is Applied

[5] Medical Observation System According to Fourth Embodiment

[5-1] Configuration of Medical Observation System According to Fourth Embodiment

[5-2] Example of Effect Exhibited by Medical Observation Device According to Fourth Embodiment When Control Method According to Present Embodiment Is Applied 2. Program According to Present Embodiment Medical Observation System According to Present Embodiment and Control Method According to Present Embodiment A control method according to the present embodiment will be described while describing an example of a medical holding device according to the present embodiment.

Hereinafter, a case where a medical holding device according to the present embodiment is an electronic-imaging-type medical observation device, that is, a case where the medical holding device is a medical observation device having an arm that supports an imaging device (an example of medical instruments) will be exemplified. Incidentally, the medical holding device according to the present embodiment is not limited to the electronic-imaging-type medical observation device. For example, the medical holding device according to the present embodiment can be applied to an arbitrary medical device having an arm that supports a medical instrument such as an optical medical observation device, an endoscope, and an endoscope holder.

In addition, hereinafter, a description will be given regarding a case where the medical holding device according to the present embodiment which functions as the medical observation device performs processing relating to the control method according to the present embodiment, that is, a case where the medical holding device according to the present embodiment functions as a medical control device will be described. Incidentally, the device functioning as the medical control device is not limited to the medical holding device according to the present embodiment in a medical observation system according to the present embodiment. For example, in the medical observation system according to the present embodiment, an arbitrary device capable of performing processing relating to the control method according to the present embodiment, such as a medical controller, can function as the medical control device.

[1] Medical Observation System According to First Embodiment

FIG. 1 is an explanatory view illustrating an example of a configuration of a medical observation system 1000 according to a first embodiment. The medical observation system 1000 includes, for example, a medical observation device 100A (an example of the medical holding device, which will be similarly applied to a medical observation devices according to other embodiments hereinafter); and a display device 200.

Incidentally, the medical observation system according to the first embodiment is not limited to the example illustrated in FIG. 1.

For example, the medical observation system according to the first embodiment may further include a medical control device (not illustrated) that controls various operations in the medical observation device 100A. As will be described later, the medical observation system 1000 illustrated in FIG. 1 illustrates an example in which the medical observation device 100A has the function of the medical control device by providing a control unit (to be described later) that performs processing relating to a control method according to the present embodiment in the medical observation device 100A.

Examples of the medical control device (not illustrated) include arbitrary instruments which can perform the processing relating to the control method according to the present embodiment such as the "medical controller", and a "computer such as a server". In addition, the medical control device may be, for example, an integrated circuit (IC) that can be incorporated into the above-described instruments.

In addition, the medical observation system according to the first embodiment may have a configuration in which a plurality of the medical observation devices 100A and the display devices 200 are provided. When the plurality of medical observation devices 100A are provided, the processing relating to the control method of the medical observation device 100A to be described later is performed in each of the medical observation devices 100A. In addition, when the medical observation system according to the first embodiment has the configuration in which the plurality of medical observation devices 100A and display devices 200 are provided, the medical observation devices 100A and the display devices 200 may be associated with each other one by one, or a plurality of medical observation devices 100A may be associated with one display device 200. When a plurality of medical observation devices 100A are associated with one display device 200, any medical imaging image captured by which of the medical observation devices 100A to be displayed on a display screen is switched for example, by performing a switching operation in the display device 200.

A modification of the medical observation system according to the first embodiment described above is similarly applied even in medical observation systems according to the other embodiments to be described later.

Hereinafter, the respective devices constituting the medical observation system 1000 will be described.

[1-1] Display Device 200

The display device 200 is a display unit in the medical observation system 1000, and corresponds to an external display device as viewed from the medical observation device 100A. The display device 200 displays various images, for example, a medical imaging image (moving image or still image) captured by the medical observation device 100A, an image relating to a user interface (UI), and the like on the display screen. In addition, the display device 200 may have a configuration capable of 3D display by an arbitrary scheme. The display on the display device 200 is controlled by, for example, the medical observation device 100A or a medical control device (not illustrated).

In the medical observation system 1000, the display device 200 is installed in any place that can be visually recognized by a person involved in surgery such as an operator in an operating room, such as a wall, a ceiling, and a floor of the operating room. Examples of the display device 200 include a liquid crystal display, an organic electro-luminescence (EL) display, and a cathode ray tube (CRT) display.

Incidentally, the display device 200 is not limited to the above-described examples.

For example, the display device 200 may be an arbitrary wearable device such as a head-mounted display and an eyewear device worn by the operator or the like on the body.

The display device 200 is driven by, for example, power supplied from an internal power supply such as a battery provided in the display device 200, or power supplied from a connected external power supply.

[1-2] Medical Observation Device 100A

The medical observation device 100A is an electronic-imaging-type medical observation device. For example, when the medical observation device 100A is used at the time of surgery, the operator (an example of the user of the medical observation device 100A) observes a surgical site (affected site) while referring to the medical imaging image, captured by the medical observation device 100A and displayed on the display screen of the display device 200, and performs various types of treatment such as procedures according to surgical operations for the surgical site.

As illustrated in FIG. 1, the medical observation device 100A includes, for example, a base 102, an arm 104A, and an imaging device 106.

In addition, the medical observation device 100A may include, for example, one or more processors (not illustrated) configured using an arithmetic circuit such as a micro processing unit (MPU), a read-only memory (ROM) (not illustrated), a random access memory (RAM) (not illustrated), a recording medium (not illustrated), and a communication device (not illustrated) although not illustrated in FIG. 1. The medical observation device 100A is driven by, for example, power supplied from an internal power supply such as a battery provided in the medical observation device 100A, or power supplied from a connected external power supply.

The processor (not illustrated) functions as a control unit (to be described later) in the medical observation device 100A. The ROM (not illustrated) stores control data such as a program and an operation parameter to be used by the processor. The RAM (not illustrated) temporarily stores a program and the like to be executed by the processor.

The recording medium (not illustrated) functions as a storage unit (not illustrated) in the medical observation device 100A. The recording medium stores, for example, data relating to the control method according to the present embodiment and various types of data such as various applications. Here, examples of the recording medium include a magnetic recording medium such as a hard disk, a non-volatile memory such as a flash memory, and the like. In addition, the recording medium may be attachable and detachable to and from the medical observation device 100A.

The communication device (not illustrated) is a communication unit provided in the medical observation device 100A, and serves to communicate with an external device such as the display device 200 in a wireless or wired manner. Here, examples of the communication device include an IEEE 802.15.1 port and a transceiver circuit (wireless communication), an IEEE 802.11 port and transceiver circuit (wireless communication), a communication antenna and an RF circuit (wireless communication), a LAN terminal and a transceiver circuit (wire communication), or the like.

[1-2-1] Base 102

The base 102 is a base of the medical observation device 100A, is connected with one end of the arm 104A, and supports the arm 104A and the imaging device 106.

In addition, the base 102 is provided with, for example, a caster, and the medical observation device 100A is grounded to a floor surface via the caster. Since the caster is provided, the medical observation device 100A can easily move on the floor surface by the caster.

[1-2-2] Arm 104A

The arm 104A is configured by coupling a plurality of links to each other by joint portions. The arm 104A has at least seven or more degrees of freedom with rotational operations on rotation axes to be described later. The seven or more degrees of freedom of the arm 104A include six degrees of freedom realized by rotational operations of six passive rotation axes and one or more degrees of freedom realized by rotational operations of one or more active rotation axes. The example illustrated in FIG. 1 is an example of a configuration having seven degrees of freedom as will be described later.

The passive rotation axis according to the present embodiment is a rotation axis that passively rotates. The passive rotation of the rotation axis includes, for example, a "rotation of the rotation axis caused by a force applied to the rotation axis" and a "rotation of the rotation axis by a passive operation of the actuator provided at the joint portion corresponding to the passive rotation axis according to a detection result of a torque applied to the rotation axis". Here, the torque applied to the rotation axis is detected by, for example, a torque sensor provided at the joint portion corresponding to the passive rotation axis. The torque sensor detects a rotational torque generated by gravity and an external force applied to the arm. Then, the actuator passively operates depending on the detected external force so as to cancel the rotational torque generated by the detected gravity.

The active rotation axis according to the present embodiment is a rotation axis that actively rotates. The active rotation of the rotation axis includes, for example, a "rotation of the rotation axis by an active operation of the actuator provided at the joint portion corresponding to the active rotation axis with the processing relating to the control method according to the present embodiment".

In addition, the arm 104A supports the imaging device 106. The imaging device 106 supported by the arm 104A is an example of the medical instrument supported by the arm 104A. The imaging device 106 supported by the arm 104A is three-dimensionally movable, and a position and a posture of the imaging device 106 after movement are held by the arm 104A.

More specifically, the arm 104A includes, for example, a plurality of joint portions 110a, 110b, 110c, 110d, 110e, 110f, and 110g and a plurality of links 112a, 112b, 112c, 112d, and 112e coupled by the joint portions 110a, 110b, 110c, 110d, 110e, 110f, and 110g. A rotatable range of each of the joint portions 110a, 110b, 110c, 110d, 110e, 110f, and 110g is arbitrarily set in a design stage, a manufacturing stage, or the like so as to realize a desired movement of the arm 104A.

That is, in the medical observation device 100A illustrated in FIG. 1, the seven degrees of freedom are realized regarding the movement of the imaging device 106 by seven rotation axes (a first axis O1, a second axis O2, a third axis O3, a fourth axis O4, a fifth axis O5, a sixth axis O6, and a seventh axis O7) corresponding to the seven joint portions 110a, 110b, 110c, 110d, 110e, 110f, and 110g constituting the arm 104A.

The first axis O1 is the first rotation axis counted from a side of the arm 104A on which the imaging device 106 is supported. The second axis O2 is the second rotation axis counted from the side of the arm 104A on which the imaging device 106 is supported. The third axis O3 is the third rotation axis counted from the side of the arm 104A on which the imaging device 106 is supported. The seventh axis O7 is the fourth rotation axis counted from the side of the arm 104A on which the imaging device 106 is supported. The fourth axis O4 is the fifth rotation axis counted from the side of the arm 104A on which the imaging device 106 is supported. The fifth axis O5 is the sixth rotation axis counted from the side of the arm 104A on which the imaging device 106 is supported. The sixth axis O6 is the seventh rotation axis counted from the side of the arm 104A on which the imaging device 106 is supported.

More specifically, the six rotation axes (the first axis O1, the second axis O2, the third axis O3, the fourth axis O4, the fifth axis O5, and the sixth axis O6) corresponding to the six joint portions 110a, 110b, 110c, 110e, 110f, and 110g function as the passive rotation axes in the medical observation device 100A illustrated in FIG. 1. Movements of six degrees of freedom including three degrees of freedom of translation and three degrees of rotation are realized in the medical observation device 100A by the six passive rotation axes (the first axis O1, the second axis O2, the third axis O3, the fourth axis O4, the fifth axis O5, and the sixth axis O6).

In addition, one rotation axis (the seventh axis O7) corresponding to one joint portion 110d functions as the active rotation axis in the medical observation device 100A illustrated in FIG. 1. That is, FIG. 1 illustrates an example in which the rotation axis functioning as the active rotation axis is the fourth rotation axis counted from the side where the imaging device 106 (the example of the medical instrument supported by the arm 104A, which will be similarly applied hereinafter) is supported. Incidentally, the rotation axis functioning as the active rotation axis in the arm 104A according to the present embodiment is not limited to the example illustrated in FIG. 1. For example, it is sufficient for the rotation axis functioning as the active rotation axis to be the fourth or subsequent active rotation axis counted from the side on which the imaging device 106 (the example of the medical instrument) is supported. Another example of the rotation axis functioning as the active rotation axis will be described later.

For example, the actuator (not illustrated) is provided at the joint portion 110d corresponding to the active rotation axis, and the seventh axis O7 corresponding to the joint portion 110d is rotated by driving the actuator. The driving of the actuator that rotates the seventh axis O7, which is the active rotation axis, is controlled by, for example, a processor that functions as a control unit to be described later or an external medical control device (not illustrated). The actuator provided at the joint portion corresponding to the active rotation axis may be an actuator included in the medical observation device 100A or an actuator outside the medical observation device 100A.

As described above, the torque sensor (not illustrated) and the actuator (not illustrated) may be provided at some or all of the joint portions 110a, 110b, 110c, 110e, 110f, and 110g corresponding to the passive rotation axes. Examples of the configuration in which the torque sensor and the actuator are provided only at some of the joint portions corresponding to the passive rotation axes include a configuration in which torque sensor and actuator are provided at each of the joint portions 110e, 110f, and 110g, and no torque sensor and no actuator are provided at the joint portions 110a, 110b, and 110c". The torque sensor provided at the joint portion corresponding to the passive rotation axis may be a torque sensor provided in the medical observation device 100A or may be a torque sensor outside the medical observation device 100A. In addition, the actuator provided at the joint portion corresponding to the passive rotation axis may be an actuator included in the medical observation device 100A or an actuator outside the medical observation device 100A.

In addition, angle sensors (not illustrated) capable of detecting rotation angles on the corresponding rotation axes are provided, respectively, at some or all of the joint portions 110a, 110b, 110c, 110e, 110f, and 110g corresponding to the passive rotation axes. The medical observation device 100A is provided with at least the angle sensor that detects a rotation angle of the second axis O2 corresponding to the joint portion 110b. The angle sensor may be an angle sensor provided in the medical observation device 100A, or may be an angle sensor outside the medical observation device 100A. Examples of the angle sensor according to the present embodiment include arbitrary sensors which can obtain a rotation angle of a rotation axis such as a rotary encoder and an angular velocity sensor.

The joint portion 110a has a substantially cylindrical shape and supports the imaging device 106 (an upper end portion of the imaging device 106 in FIG. 1) so as to be rotatable about the rotation axis (the first axis O1) parallel to a central axis of the imaging device 106 at a distal end portion of the joint portion 110a (a lower end portion in FIG. 1). Here, the first axis O1 is configured to coincide with an optical axis of the imaging device 106 in the medical observation device 100A illustrated in FIG. 1. In other words, the first axis O1 is coaxial with the optical axis of the imaging device 106. That is, as the imaging device 106 is rotated about the first axis O1 illustrated in FIG. 1, the medical imaging image captured by the imaging device 106 becomes an image whose field of view is changed to be rotated. Incidentally, it is a matter of course that the configuration of the medical observation device 100A is not limited to the configuration in which the first axis O1 is coaxial with the optical axis of the imaging device 106.

The link 112a is a substantially rod-shaped member and fixedly supports the joint portion 110a. The link 112a is extended, for example, in a direction orthogonal to the first axis O1 and is connected to the joint portion 110b.

The joint portion 110b has a substantially cylindrical shape, and supports the link 112a so as to be rotatable about the rotation axis (the second axis O2) orthogonal to the first axis O1. In addition, the link 112b is fixedly connected to the joint portion 110b.

The link 112b is a substantially L-shaped member whose one side extends in a direction orthogonal to the second axis O2, and the joint portion 110b and the joint portion 110c are connected to the link 112b.

The joint portion 110c has a substantially cylindrical shape, and supports the link 112b so as to be rotatable about at least the rotation axis (the third axis O3) orthogonal to the second axis O2. In addition, the joint portion 110c is connected to the joint portion 110d via the link 112c.

Here, as the distal end side of the arm 104A (the side on which the imaging device 106 is provided) is rotated about the second axis O2 and the third axis O3, the imaging device 106 can be moved such that the imaging device 106 rotates. Incidentally, when the rotation about the second axis O2 and the third axis O3 is small, the field of view of the medical imaging image seems to move in a plane. In addition, the field of view of the medical imaging image rotates as the imaging device 106 rotates about the first axis O1 in the medical observation device 100A as described above.

Thus, it is possible to say that the first axis O1, the second axis O2, and the third axis O3 (the first rotation axis, the second rotation axis, and the third rotation axis counted from the side of the arm 104A on which the imaging device 106 is supported) are the rotation axes relating to a tilting operation of the imaging device 106 in the medical observation device 100A. The center of gravity of each link connected to each of the rotation axes is placed on the rotation axis of each of the first axis O1, the second axis O2, and the third axis O3. With the configuration in which the center of gravity is placed on the rotation axis of each of the first axis O1, the second axis O2, and the third axis O3, the actuator configured to cancel a rotational moment generated by the gravity becomes unnecessary.

The joint portion 110d is connected to the joint portion 110c via the link 112c, and supports the link 112b so as to be rotatable about the rotation axis (the seventh axis O7) orthogonal to the third axis O3. As described above, the seventh axis O7 corresponding to the joint portion 110d is the active rotation axis in the example illustrated in FIG. 1.

The link 112c is connected to the link 112b via the joint portion 110c and connected to the link 112d via the joint portion 110e.

The joint portion 110e supports the link 112c so as to be rotatable about the rotation axis (the fourth axis O4) orthogonal to the third axis O3. The link 112d is connected to the joint portion 110e.

The link 112d is connected to the link 112c via the joint portion 110e and connected to the link 112e via the joint portion 110f.

The joint portion 110f supports one end of the link 112d so as to be rotatable about the rotation axis (the fifth axis O5) parallel to the fourth axis O4. In addition, one end of the link 112e is connected to the joint portion 110f.

Here, the fourth axis O4 and the fifth axis O5 are the rotation axes that can move the imaging device 106 in the vertical direction. As the distal end side of the arm 104A (the side on which the imaging device 106 is provided) rotates about the fourth axis O4 and the fifth axis O5, a position of the imaging device 106 in the vertical direction is changed. Thus, the distal end side of the arm 104A (the side on which the imaging device 106 is provided) rotates about the fourth axis O4 and the fifth axis O5, it is possible to change a distance between the imaging device 106 and an observation target such as a surgical site of a patient.

The link 112e is a member configured by combining a substantially L-shaped first member which has one side extending in the vertical direction and the other side extending in the horizontal direction and a rod-shaped second member extending vertically downward from a portion extending in the horizontal direction of the first member. The joint portion 110f is fixedly connected to a portion extending in the vertical direction of the first member of the link 112e. In addition, the joint portion 110g is connected to the second member of the link 112e.

The link 112e and the base 102 are connected to the joint portion 110g. The joint portion 110g supports the link 112e so as to be rotatable about the rotation axis (the sixth axis O6) parallel to the vertical direction. Here, as the link 112e rotates about the sixth axis O6, the imaging device 106 moves in the horizontal direction. In addition, the fourth axis O4 and the fifth axis O5 are the rotation axes that can move the imaging device 106 in the vertical direction as described above. Thus, it is possible to say that the fourth axis O4, the fifth axis O5, and the sixth axis O6 (three rotation axes other than the first axis O1, the second axis O2, and the third axis O3 among the six passive rotation axes of the arm 104A) are the passive rotation axis that defines a three-dimensional position of the imaging device 106 in the medical observation device 100A.

As the arm 104A has the above-described configuration, seven degrees of freedom regarding the movement of the imaging device 106 are realized in the medical observation device 100A.

Incidentally, the configuration of the arm 104A is not limited to the example described above.

For example, some or all of the joint portions 110a, 110b, 110c, 110d, 110e, 110f, and 110g of the arm 104A are provided with a brake (not illustrated) that restricts a rotation on the corresponding rotation axis. Examples of the configuration in which the brake is provided only at some of the joint portions of the arm 104A include a "configuration in which the brake is provided at the joint portions 110a, 110b, 110c, and 110d and no brake is provided at the joint portions 110e, 110f, and 110g". Examples of the brake according to the present embodiment include a brake of an arbitrary scheme, such as a mechanically driven brake and an electrically driven electromagnetic brake.

The driving of the above-described brake (not illustrated) is controlled by, for example, the processor that functions as the control unit to be described later or the external medical control device (not illustrated). As the driving of the above-described brake is controlled, an operation mode of the arm 104A is set in the medical observation device 100A. Examples of the operation mode of the arm 104A include an entirely fixed mode, a partially fixed mode, and a free mode. Incidentally, the brake that regulates the rotation of the seventh axis, which is the active rotation axis regulates the rotation of the seventh axis, for example, regardless of the set operation mode unless the regulation is released by the processing relating to the control method according to the present embodiment. That is, the operation mode of the arm 104A defines, for example, the operation of the brake provided on the passive rotation axis.

Here, the entirely fixed mode according to the present embodiment is an operation mode in which the rotations on all the passive rotation axes are restricted by brakes, for example, when the brakes (not illustrated) are provided at joint portions corresponding to all the passive rotation axes of the arm 104A. As the rotations of all the passive rotation axes of the arm 104A are regulated by the brakes, a position and a posture of the imaging device 106 are fixed. That is, as the arm 104A is set to the entirely fixed mode, the operation state of the medical observation device 100A is set to a fixed state where the position and the posture of the imaging device 106 are fixed.

In addition, the partially fixed mode according to the present embodiment is an operation mode in which the rotations of the passive rotation axes corresponding to some joint portions are regulated by brakes, for example, using the brakes (not illustrated) provided at some joint portions among the joint portions corresponding to the passive rotation axes of the arm 104A. For example, an operation mode in the "case where the rotation is regulated by the brake in the configuration in which the brake is provided only at some joint portions corresponding to the passive rotation axes of the arm 104A" corresponds to the partially fixed mode. As the rotations of some passive rotation axes of the arm 104A are regulated by the brakes, the position and the posture of the imaging device 106 are partially fixed. As an example, when the partially fixed mode is set, the rotational operations on the first axis O1, the second axis O2, and the third axis O3 are possible, and the rotational operations of the other passive rotation axes are restricted. Incidentally, it is a matter of course that the example of the restriction in the case where the partially fixed mode is set is not limited to the example described above.

In addition, the free mode according to the present embodiment is an operation mode in which the respective passive rotation axes provided on the arm 104A can freely rotate as the above-described brakes are released. For example, in the free mode, it is possible to adjust the position and the posture of the imaging device 106 by a direct operation by an operator. Here, examples of the direct operation according to the present embodiment include an "operation in which the operator grips the imaging device 106 by a hand and directly moves the imaging device 106".

[1-2-3] Imaging Device 106

The imaging device 106 is supported by the arm 104A, and captures, for example, an image of an observation target such as a surgical site of a patient. The imaging in the imaging device 106 is controlled by, for example, the processor that functions as the control unit to be described later or the external medical control device (not illustrated).

The imaging device 106 has a configuration corresponding to, for example, an electronic imaging microscope.

FIGS. 2A and 2B are explanatory diagrams for describing an example of the configuration of the imaging device 106 provided in the medical observation device 100A according to the present embodiment. FIGS. 2A and 2B illustrate a case where the first axis O1 is coaxial with the optical axis of the imaging device 106, and the optical axis of the imaging device 106 is directed downward in the vertical direction.

The imaging device 106 illustrated in FIGS. 2A and 2B includes, for example, an imaging member 120 and a cylindrical member 122 having a substantially cylindrical shape, and the imaging member 120 is provided inside the cylindrical member 122.

For example, a cover glass (not illustrated) configured to protect the imaging member 120 is provided on an aperture surface of a lower end (the lower end in FIGS. 2A and 2B) of the cylindrical member 122.

In addition, for example, a light source (not illustrated) is provided inside the cylindrical member 122, and illumination light is emitted to a subject from the light source through the cover glass at the time of imaging. Reflected light (observation light) from the subject irradiated with the illumination light is incident on the imaging member 120 through the cover glass (not illustrated) so that the imaging member 120 obtains an image signal (an image signal representing a medical imaging image) representing the subject.

As the imaging member 120, it is possible to apply configurations used in various known electronic imaging microscopes.

As an example, the imaging member 120 is constituted by, for example, an optical system 120a and an image sensor 120b including an imaging element which captures an image of an observation target by light passing through the optical system 120a. The optical system 120a is constituted by, for example, one or more lenses such as an objective lens, a zoom lens, and a focus lens, and an optical element such as a mirror. Examples of the image sensor 120b include an image sensor using a plurality of imaging elements such as a complementary metal oxide semiconductor (CMOS) and a charge coupled device (CCD).

The image sensor 120b may have the number of pixels capable of so-called high-resolution imaging, such as 4K and 8K. Since the imaging member 120 is configured to be capable of imaging at high resolution, it is possible to display an image on the display device 200 having a display screen, which is a large screen of 50 inches or more, for example, while securing a predetermined resolution (for example, full HD image quality or the like), and thus, the visibility of a viewer of the display screen is improved. In addition, it is possible to secure a predetermined resolution even if an imaging image is enlarged by an electronic zoom function and displayed on the display screen of the display device 200 since the imaging member 120 is configured to be capable of imaging at high resolution. Furthermore, when the predetermined resolution is secured using the electronic zoom function, it is possible to suppress the performance of an optical zoom function in the imaging member 120, and thus, the optical system of the imaging member 120 can be simplified. Further, the imaging device 106 can be configured to be smaller since the optical system of the imaging member 120 is simplified.

The imaging member 120 functions as a so-called stereo camera by having two or more imaging devices each of which is constituted by the optical system 120a and the image sensor 120b.

The imaging device constituting the imaging member 120 is equipped with one or more functions generally provided in an electronic imaging microscope unit such as a zoom function (an optical zoom function and/or an electronic zoom function), and an auto focus (AF) function.

The imaging device 106 is provided with various operation devices configured to control operations of the imaging device 106, for example. The imaging device 106 is provided with a zoom switch 124, a focus switch 126, and an operation mode setting switch 128, for example, in FIGS. 2A and 2B. Incidentally, it is a matter of course that positions and shapes at which the zoom switch 124, the focus switch 126, and the operation mode setting switch 128 are provided are not limited to the example illustrated in FIGS. 2A and 2B.

The zoom switch 124 and the focus switch 126 are examples of an operation device configured to adjust an imaging condition in the imaging device 106.

The zoom switch 124 includes, for example, a zoom-in switch 124a that increases a zoom magnification (magnification power) and a zoom out switch 124b that decreases the zoom magnification. The zoom magnification is adjusted by operating the zoom switch 124, whereby the zoom is adjusted.

The focus switch 126 includes, for example, a distant-view focus switch 126a that increases a focal distance to the observation target (subject) and a near-view focus switch 126b which decreases the focal distance to observation object. The focal distance is adjusted by operating the focus switch 126, whereby the focus is adjusted.

The operation mode setting switch 128 is an example of an operation device configured to set the operation mode of the arm 104A in the imaging device 106. The operation mode setting switch 128 is operated to change the operation mode of the arm 104A. Examples of the operation mode to be changed by operating the operation mode setting switch 128 include the entirely fixed mode and the free mode. In addition, the operation mode may be changed to any of the entirely fixed mode, the partially fixed mode, and the free mode by operating the operation mode setting switch 128.

An example of the operation on the operation mode setting switch 128 is an operation of pressing the operation mode setting switch 128. For example, the operation mode of the arm 104A becomes the free mode while the operator is pressing the operation mode setting switch 128, and the operation mode of the arm 104A becomes the entirely fixed mode when the operator does not press the operation mode setting switch 128. In addition, for example, "when the operator presses, releases, and presses again the operation mode setting switch 128 within a predetermined set time" the operation mode of the arm 104A becomes the partially fixed mode while the operation mode setting switch 128 is being pressed again. Incidentally, it is a matter of course that the example of the operation on the operation mode setting switch 128 and the example of the operation mode corresponding to the operation are not limited to the examples illustrated above.

The imaging device 106 is provided with, for example, an anti-slip member 130 and a protruding member 132 in order to further enhance the operability and convenience when an operator who performs an operation on various operation devices performs the operation.

The anti-slip member 130 is a member provided to prevent a slip from an operating body, for example, when the operator operates the cylindrical member 122 with the operating body such as a hand. The anti-slip member 130 is formed using, for example, a material having a large coefficient of friction, and has a less slippery structure such as unevenness.

The protruding member 132 is a member provided to prevent an operating body from blocking the field of view of the optical system 120a when the operator operates the cylindrical member 122 with the operating body such as a hand or prevent the cover glass from being dirty due to touch of the operating body on the cover glass (not illustrated) at the time of performing the operation with the operating body.

Incidentally, it is a matter of course that positions and shapes at which the anti-slip member 130 and the protruding member 132 are provided are not limited to the example illustrated in FIGS. 2A and 2B. In addition, one or both of the anti-slip member 130 and the protruding member 132 are not necessarily provided in the imaging device 106.

The image signal (image data) generated by imaging in the imaging device 106 is subjected to image processing, for example, in the processor that functions as the control unit to be described later. Examples of the image processing according to the present embodiment include one or more types of processing among various types of processing such as gamma correction, white balance adjustment, enlargement or reduction of an image according to the electronic zoom function, and inter-pixel correction. Incidentally, when the medical observation system according to the present embodiment includes a medical control device (not illustrated) that controls various operations in the medical observation device 100A, the image processing according to the present embodiment may be performed in the medical control device.

The medical observation device 100A transmits, for example, a display control signal and the image signal having been subjected to the above-described image processing to the display device 200.

As the display control signal and the image signal are transmitted to the display device 200, a medical imaging image in which an image of an observation target has been captured (for example, an imaging image in which an image of a surgical site has been captured) is enlarged or reduced to a desired magnification by one or both of the optical zoom function and the electronic zoom function, and then, displayed on the display screen of the display device 200.

The medical observation device 100A has, for example, a hardware configuration illustrated with reference to FIG. 1 and FIGS. 2A and 2B.

Incidentally, the hardware configuration of the medical observation device according to the present embodiment is not limited to the configuration illustrated with reference to FIG. 1 and FIGS. 2A and 2B.

For example, the medical observation device according to the present embodiment does not necessarily include the base 102, and the arm 104A may be directly attached to the ceiling or wall of an operating room or the like. For example, when the arm 104A is attached to the ceiling, the medical observation device according to the present embodiment is configured such that the arm 104A is suspended from the ceiling.

In addition, FIG. 1 illustrates the example in which the arm 104A is configured such that seven degrees of freedom (six degrees of freedom with six passive rotation axes and one degree of freedom with one active rotation axis) are realized regarding the driving of the imaging device 106, but the configuration of the arm 104A is not limited to the configuration in which the degree of freedom regarding the driving the imaging device 106 is seven. For example, the arm 104A may have eight or more degrees of freedom by having two or more active rotation axes. When the arm 104A has the eight or more degrees of freedom, each active rotation axis is the fourth or subsequent rotation axis counted from the side on which the imaging device 106 is supported.

In addition, FIG. 1 and FIGS. 2A and 2B illustrate the example in which various operation devices to control the operations of the imaging device 106 are provided in the imaging device 106, but some or all of the operation devices illustrated in FIG. 1 and FIGS. 2A and 2B are not necessarily provided in the imaging device 106. As one example, the various operation devices to control the operations of the imaging device 106 may be provided in parts other than the imaging device 106 constituting the medical observation device according to the present embodiment. In addition, as another example, the various operation devices to control the operations of the imaging device 106 may be arbitrary external operation devices such as a foot switch and a hand switch such as a remote controller.

In addition, the imaging device 106 may be configured to be capable of switching among a plurality of observation modes. Examples of the observation mode according to the present embodiment include an observation mode in which imaging is performed with natural light, an observation mode in which imaging is performed with special light, an observation mode in which imaging is performed using an image enhancement observation technique, and the like. Examples of the special light according to the present embodiment include light of a specific wavelength band, such as light of a near infrared wavelength band and light of a fluorescence wavelength band of fluorescence observation using 5-aminolevulinic acid (5-ALA).

An example of the configuration of the imaging device 106 capable of switching among the plurality of observation modes is a "configuration in which a filter that transmits light of a specific wavelength band and does not transmit light of other wavelength bands and a moving mechanism that selectively disposes the filter on a light path are provided". Examples of the specific wavelength band transmitted by the filter according to the present embodiment include a wavelength band of near infrared light (for example, a wavelength band of about 0.7 [micrometer] to 2.5 [micrometer]), a fluorescence wavelength band by fluorescence observation using 5-ALA (for example, a wavelength band of about 0.6 [micrometer] to 0.65 [micrometer]), a fluorescent wavelength band of indocyanine green (ICG) (for example, a wavelength band of about 0.82 [micrometer] to 0.85 [micrometer]), and the like.

Incidentally, the imaging device 106 may be provided with a plurality of filters having different wavelength bands to be transmitted. In addition, the example in which the filter is disposed on the light path to perform imaging with light of the specific wavelength band has been illustrated in the above description, but it is a matter of course that the configuration of the imaging device 106 configured to perform imaging with light of the specific wavelength band is not limited to the example illustrated above.

Figure 3:
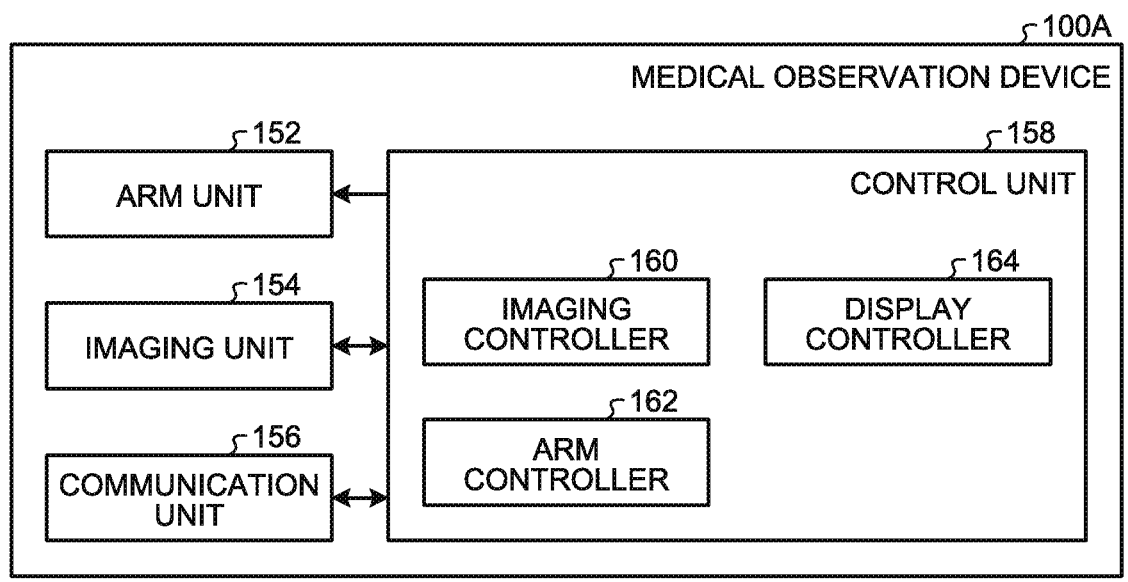
FIG. 3 is a functional block diagram illustrating an example of the configuration of the medical observation device according to the first embodiment.

Next, the medical observation device 100A illustrated in FIG. 1 will be described using a functional block. FIG. 3 is a functional block diagram illustrating an example of the configuration of the medical observation device 100A according to the present embodiment.

The medical observation device 100A includes, for example, an arm unit 152, an imaging unit 154, a communication unit 156, and a control unit 158.

The arm unit 152 is configured using the arm 104A and supports the imaging device 106 that constitutes the imaging unit 154.

The imaging unit 154 is configured using the imaging device 106, and captures an image of an observation target. The imaging in the imaging unit 154 is controlled by, for example, the control unit 158.

The communication unit 156 is a communication unit provided in the medical observation device 100A, and serves to communicate with an external device such as the display device 200 in a wireless or wired manner. The communication unit 156 includes, for example, the above-described communication device (not illustrated). The communication in the communication unit 156 is controlled by, for example, the control unit 158.

The control unit 158 is configured using, for example, the processor (not illustrated) described above, and serves to control the entire medical observation device 100A. In addition, the control unit 158 also plays a leading role in performing the processing relating to the control method to be described later. Incidentally, the processing relating to the control method in the control unit 158 may be distributed and performed by a plurality of processing circuits (for example, a plurality of processors).

More specifically, the control unit 158 includes, for example, an imaging controller 160, an arm controller 162, and a display controller 164.

The imaging controller 160 controls the imaging device 106 that constitutes the imaging unit 154. Examples of the control of the imaging device 106 include control of one or more functions generally provided in an electronic imaging microscope unit, such as control of an AF function including at least a zoom function (an optical zoom function and an electronic zoom function).

The arm controller 162 controls driving of the arm 104A that constitutes the arm unit 152. An example of the control of driving of the arm 104A is "to apply a control signal for controlling driving to the actuator (not illustrated) corresponding to the joint portion 110d corresponding to the active rotation axis".

In addition, the arm controller 162 serves to perform the processing relating to the control method to be described later. An example of the processing relating to the control method according to the present embodiment will be described later.

The display controller 164 transmits, for example, a display control signal and an image signal to the communication device (not illustrated) constituting the communication unit 156, and transmits the display control signal and the image signal to the display device 200 to control the display on the display device 200. Incidentally, the control of communication in the communication unit 156 may be performed by a communication controller (not illustrated) that constitutes the control unit 158.

The control unit 158 plays a leading role in performing the processing relating to the control method according to the present embodiment, for example, by including the arm controller 162. In addition, the control unit 158 also serves to control the entire medical observation device 100A, for example, by including the imaging controller 160, the arm controller 162, and the display controller 164.

Incidentally, a functional configuration of the control unit 158 is not limited to the example illustrated in FIG. 3.

For example, the control unit 158 may have an arbitrary configuration in accordance with how to separate the functions of the medical observation device 100A, such as a configuration in accordance with how to separate the processes relating to the control method according to the present embodiment.

The medical observation device 100A performs the process relating to the control method according to the present embodiment to be described later, for example, by the configuration illustrated in FIG. 3.

Incidentally, the functional configuration of the medical observation device according to the present embodiment is not limited to the configuration illustrated in FIG. 3.

For example, some or all of the imaging controller 160, the arm controller 162, and the display controller 164 illustrated in FIG. 3 can be provided separately from the control unit 158 (for example, can be realized by another processing circuit) in the medical observation device according to the present embodiment.

In addition, the functional configuration configured to realize the processing relating to the control method according to the present embodiment in the medical observation device according to the present embodiment is not limited to the configuration illustrated in FIG. 3, and the medical observation device according to the present embodiment, for example, can have a functional configuration in accordance with how to separate the processing relating to the control method according to the present embodiment.

In addition, the medical observation device according to the present embodiment is an example of the medical holding device according to the present embodiment as described above, and the imaging device 106 supported by the arm 104A constituting the arm unit 152 may be a removable external imaging device. In addition, the medical observation device according to the present embodiment does not include the imaging unit 154 in a state where the external imaging device has been removed.

In addition, for example, when communicating with an external device through an external communication device having the same function and configuration as the communication unit 156, the medical observation device according to the present embodiment does not necessarily include the communication unit 156.

In addition, when the medical observation system according to the present embodiment is configured to have a medical control device (not illustrated) and the medical observation device according to the present embodiment is controlled by the medical control device, the medical observation device according to the present embodiment does not necessarily include the control unit 158.

Here, the medical control device (not illustrated) includes, for example, a control unit having the same function and configuration as the control unit 158 to perform the processing relating to the control method according to the present embodiment to be described later, and control operations of the respective components such as the arm unit 152 and the imaging unit 154 provided in the medical observation device according to the present embodiment. The medical control device performs communication with the medical observation device according to the present embodiment via an internally provided communication device or a connected external communication device to control the operations of the respective components provided in the medical observation device according to the present embodiment.

Furthermore, when the medical observation system according to the present embodiment is configured to have a medical control device (not illustrated) and the medical observation device according to the present embodiment is controlled by the medical control device, the medical observation device according to the present embodiment can also be configured so as not to have some functions of the control unit 158.

The above-described functional configuration of the medical observation device 100A (including the modification) is also applied to a medical observation device constituting a medical observation system according to another embodiment to be described later.

[2] Control Method According to Present Embodiment

Next, the control method according to the present embodiment will be described. Hereinafter, a case where the processing relating to the control method according to the present embodiment is performed by the medical observation device 100A constituting the medical observation system 1000 according to the first embodiment (more specifically, for example, the arm controller 162 provided in the control unit 158) will be exemplified. Incidentally, the processing relating to the control method according to the present embodiment may be performed by the medical control device (not illustrated) in the medical observation system according to the present embodiment as described above.

[2-1] Outline of Control Method According to Present Embodiment

When the operation mode of the arm 104A is the free mode, a user of the medical observation device 100A can freely move a position of the imaging device 106. However, there is a case where the degrees of freedom of the arm 104A decreases depending on a posture of the arm 104A supporting the imaging device 106 as described above. When the degree of freedom of the arm 104A decreases, a "situation where it is difficult to move the imaging device to capture a desired imaging range unless the user manually change the posture of the arm" is likely to occur. Further, when the above situation occurs, the convenience of the user using the medical observation device is likely to deteriorate.

Figure 4A:
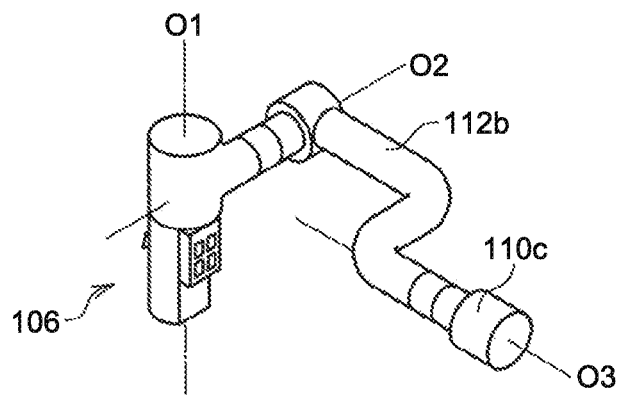
FIGS. 4A to 4C are explanatory views for describing an outline of a control method according to the present embodiment.
Figure 4B:
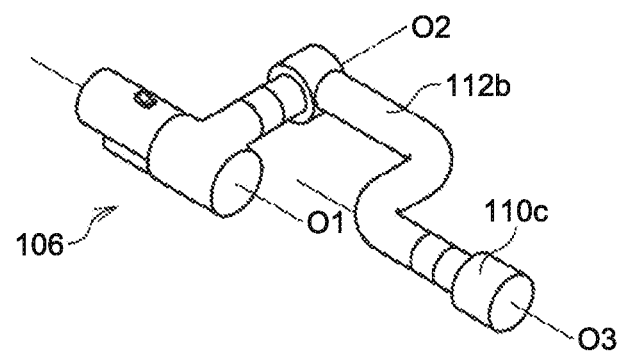
Figure 4C:
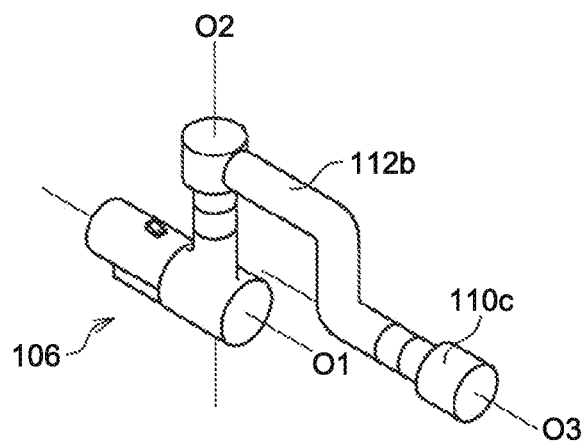

FIGS. 4A to 4C are explanatory views for describing an outline of the control method according to the present embodiment, and illustrate a part of the arm 104A from the side on which the imaging device 106 is supported to the third axis O3. FIG. 4A illustrates a first example of the posture of the arm 104A. FIG. 4B illustrates a second example of the posture of the arm 104A, and FIG. 4C illustrates a third example of the posture of the arm 104A.

In the posture according to the first example illustrated in FIG. 4A, the first axis O1, the second axis O2, and the third axis O3 are in states of being orthogonal to each other. At this time, a medical observation image is rotated by the rotational operation on the first axis O1, and an imaging range of the imaging device 106 moves in an up-down direction (the vertical direction, which will be similarly applied hereinafter) by the rotational operation on the second axis O2. The imaging range of the imaging device 106 moves in a left-right direction (a direction orthogonal to the vertical direction, which will be similarly applied hereinafter) by the rotational operation on the third axis O3. In the posture according to the first example illustrated in FIG. 4A, the degree of freedom does not decrease, and the degree of freedom is not insufficient.

The posture according to the second example illustrated in FIG. 4B is a posture obtained by rotating the second axis O2 by 90[°] from the posture according to the first example illustrated in FIG. 4A. At this time, the medical observation image is rotated by the rotational operation on the first axis O1 and the rotational operation on the third axis O3. In addition, in the case where the imaging range of the imaging device 106 is moved in the up-down direction by the rotational operation on the second axis O2, there is no movement component causing the imaging range of the imaging device 106 to move in the left-right direction in the posture according to the second example illustrated in FIG. 4B. That is, the degree of freedom in the posture according to the second example illustrated in FIG. 4B is lower than the degree of freedom in the posture according to the first example illustrated in FIG. 4A, and the degree of freedom is insufficient.

The posture according to the third example illustrated in FIG. 4C is a posture obtained by rotating the first axis O1 and the third axis O3 by 90[°] from the posture according to the second example illustrated in FIG. 4B. At this time, the medical observation image is rotated by the rotational operation on the first axis O1 and the rotational operation on the third axis O3, which is similar to the posture according to the second example illustrated in FIG. 4B. In addition, when the imaging range of the imaging device 106 moves in the left-right direction by the rotational operation on the second axis O2, there is no movement component causing the imaging range of the imaging device 106 to move in the up-down direction in the posture according to the third example illustrated in FIG. 4C. That is, the degree of freedom in the posture according to the third example illustrated in FIG. 4C is lower than the degree of freedom in the posture according to the first example illustrated in FIG. 4A, and the degree of freedom is insufficient.

For example, in the case of the posture according to the second example illustrated in FIG. 4B or the posture according to the third example illustrated in FIG. 4C, a desired degree of freedom in rotation can be obtained by relatively rotating the second axis O2 if the user such as an operator manually rotates the link 112b about the third axis O3. However, there is a case where the user needs to perform the operation using both hands when manually rotating the link 112b about the third axis O3, which may cause the user to feel annoyed.

Therefore, the medical observation device 100A controls the operation of the arm 104A to automatically secure the degree of freedom in order to prevent the posture of the arm 104A from being in a predetermined state.

For example, when the operation mode of the arm 104A is the free mode, the medical observation device 100A controls the operation of the arm 104A in accordance with the posture of the arm 104A. Incidentally, the medical observation device 100A may control the operation of the arm 104A in accordance with the posture of the arm 104A regardless of the operation mode of the arm 104A.

The predetermined state according to the present embodiment is a state where some degrees of freedom are lost depending on the posture of the arm 104A. Specifically, the predetermined state is a unique state where the number of degrees of freedom realized by the rotational operation of each of the first axis O1, the second axis O2, and the third axis O3 decreases. In other words, the predetermined state of the posture of the arm 104A refers to, for example, a "state where the first axis O1 is present in a plane defined by the second axis O2 and the third axis O3" or a "state where the first axis O1 is present in a plane parallel to the plane defined by the second axis O2 and the third axis O3" as in the posture according to the second example illustrated in FIG. 4B or the posture according to the third example illustrated in FIG. 4C.

As illustrated in FIG. 4B and FIG. 4C, the state where the first axis O1 is present on the plane defined by the second axis O2 and the third axis O3" or the "state where the first axis O1 is present on the plane parallel to the plane defined by the second axis O2 and the third axis O3" corresponds to the predetermined state. That is, when the posture of the arm 104A is in the predetermined state, an angle between the first axis O1 and the third axis O3 is 0 [°].

In addition, a rotation angle of the second axis O2 corresponds to an angle formed between the first axis O1 and the third axis O3 (which will be similarly applied hereinafter), for example, as illustrated in FIG. 1. That is, when the posture of the arm 104A is in the predetermined state, the rotation angle of the second axis O2 is 0 [°].

For example, when the posture of the arm 104A approaches the predetermined state, the medical observation device 100A secures the degree of freedom by rotating the active rotation axis so as to avoid the predetermined state. The case where the posture of the arm 104A approaches the predetermined state indicates a case where the posture of the arm 104A is likely to be in the predetermined state.

For example, the medical observation device 100A determines whether the posture of the arm 104A approaches the predetermined state based on a detection result of an angle sensor (not illustrated) that detects the rotation angle of the second axis O2 corresponding to the joint portion 110b. For example, when the rotation angle of the second axis O2 detected at a certain point in time is included in the first range, the medical observation device 100A determines that the posture of the arm 104A approaches the predetermined state. In addition, for example, when it is estimated that the rotation angle of the second axis O2 to be detected at a point in time in the future is included in the first range based on the rotation angle of the second axis O2 detected at a point in time and a temporal change of the rotation angle of the second axis O2, the medical observation device 100A can also determine that the posture of the arm 104A approaches the predetermined state.

As described above, the case where the posture of the arm 104A is in the predetermined state corresponds to the case where the rotation angle of the second axis O2 is 0 [°]. Thus, examples illustrated below can be given as the first range according to the present embodiment. Here, E1 and E2 are "0" or a "real number larger than 0" set in a design stage or the like. A value of E1 and a value of E2 may be identical or different.

$0-E1<(\text{Rotation Angle of Second Axis } O2)<0+E2$ $0-E1\leq(\text{Rotation Angle of Second Axis } O2)<0+E2$ $0-E1<(\text{Rotation Angle of Second Axis } O2)\leq0+E2$ $0-E1\leq(\text{Rotation Angle of Second Axis } O2)\leq0+E2$ Incidentally, a method of determining that the posture of the arm 104A approaches the predetermined state is not limited to the example described above.

For example, when an angle sensor (not illustrated) that detects a rotation angle of each of the first axis O1 to the seventh axis O7 (examples of all the passive rotation axes and all the active rotation axes) is provided, it is possible to identify the posture of the arm 104A (or estimate the posture of the arm 104A, which will be similarly applied hereinafter) based on the detected rotation angle. Thus, the medical observation device 100A can determine whether the posture of the arm 104A approaches the predetermined state, for example, by identifying the posture of the arm 104A. Incidentally, a method of identifying the posture of the arm 104A (or a method of estimating the posture of the arm 104A) is not limited to the example described above, and the medical observation device 100A may identify the posture of arm 104A using an arbitrary method that can identify the posture of arm 104A.

Hereinafter, the "case where the medical observation device 100A determines whether the posture of the arm 104A approaches the predetermined state based on a detection result of an angle sensor (not illustrated) that detects the rotation angle of the second axis O2" will be exemplified.

When it is determined that the posture of the arm 104A approaches the predetermined state, the medical observation device 100A operates an actuator (not illustrated) provided at the joint portion 110d corresponding to the seventh axis O7, which is the active rotation axis, to rotate the seventh axis O7, thereby avoiding the predetermined state.

Incidentally, the control of the active rotation axis in the medical observation device 100A is not limited to the example described above. For example, the medical observation device 100A can avoid the predetermined state by rotating the active rotation axis such that the posture of the arm 104A is maintained, for example.

As the predetermined state is avoided by controlling the operation of the arm 104A as described above, the degree of freedom of the arm 104A is automatically secured, and thus, the annoyance felt by the user as described above is reduced. Therefore, the medical observation device 100A can improve the convenience of the user.

[2-2] Processing Relating to Control Method According to Present Embodiment

Next, the processing relating to the control method according to the present embodiment will be more specifically described by exemplifying the case of being applied to the medical observation device 100A having the configuration illustrated in FIG. 1. As described above, the processing relating to the control method is performed, for example, by the arm controller 162 in the medical observation device 100A.

As described above, the medical observation device 100A rotates the active rotation axis such that the posture of the arm 104A is prevented from being in the predetermined state. Specifically, for example, the medical observation device 100A performs a process according to a first example illustrated in the following (A) or a process according to a second example illustrated in the following (B) to avoid the predetermined state.

(A) First Example of Processing Relating to Control Method

The medical observation device 100A determines whether the posture of the arm 104A approaches the predetermined state based on a detection result of the angle sensor (not illustrated) that detects the rotation angle of the second axis O2. Then, when determining that the posture of the arm 104A approaches the predetermined state, the medical observation device 100A rotates the active rotation axis. The medical observation device 100A rotates the active rotation axis such that the rotation angle of the second axis O2 is not included in the set first range. As described above, the medical observation device 100A determines whether the posture of the arm 104A approaches the predetermined state based on the detected rotation angle of the second axis O2, and rotates the active rotation axis when determining that the posture of the arm 104A approaches the predetermined state.

Figure 5A:
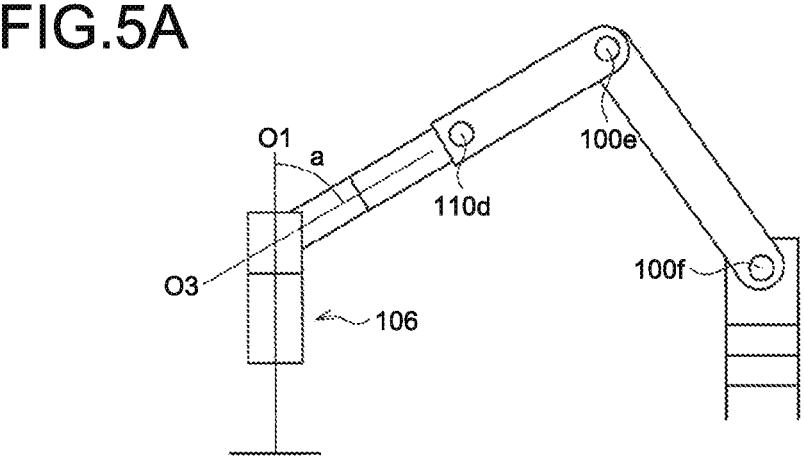
FIGS. 5A to 5C are explanatory views illustrating an example of an operation of an arm according to a first example of processing relating to the control method of the present embodiment.
Figure 5B:
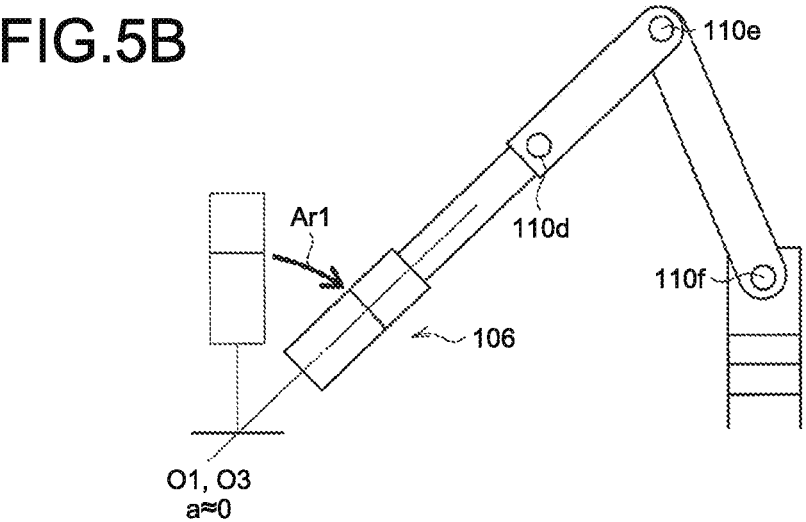
Figure 5C:
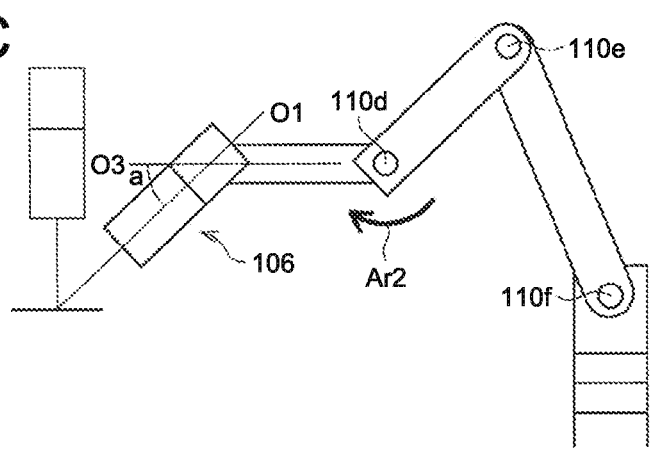

FIGS. 5A to 5C are explanatory views illustrating an example of the operation of the arm 104A according to the first example of the processing relating to the control method of the embodiment. FIGS. 5A to 5C illustrate a part of the arm 104A from the side on which the imaging device 106 is supported to the joint portion 110f corresponding to the fifth axis O5. FIG. 5A illustrates an example of the posture of the arm 104A when it is not determined that the posture approaches the predetermined state. FIG. 5B illustrates an example of the arm 104A in which the posture is in the predetermined state. FIG. 5C illustrates an example of the posture of the arm 104A when the active rotation axis rotates so as to avoid the predetermined state. In FIG. 5A, FIG. 5B, and FIG. 5C, "a" indicates an angle formed between the first axis O1 and the third axis O3. As described above, the angle a formed between the first axis O1 and the third axis O3 corresponds to the rotation angle of the second axis O2 detected by the angle sensor.

When the posture of the arm 104A changes as indicated by an arrow Ar1 in FIG. 5B from the posture illustrated in FIG. 5A, the angle a formed between the first axis O1 and the third axis O3 gradually decreases to be 0 [°] eventually. As described above, the case where the angle a formed between the first axis O1 and the third axis O3 is 0 [°] is the case where the posture of the arm 104A is in the predetermined state, and at this time, the entire arm 104A is in a state of losing one degree of freedom as a whole. That is, when the angle a formed between the first axis O1 and the third axis O3 is 0 [°], there is a direction in which the imaging device 106 supported by the arm 104A is hardly moved.

Therefore, when it is determined that the medical observation device 100A approaches the predetermined state based on the angle a formed between the first axis O1 and the third axis O3, the seventh axis O7, which is the active rotation axis, is rotated as indicated by an arrow Ar2 in FIG. 5C.

Specifically, the medical observation device 100A rotates the seventh axis O7 which is the active rotation axis, such that the third axis O3, which is the passive rotation axis, becomes horizontal. Here, the state where the third axis O3 becomes horizontal include a "state where the third axis O3 is completely horizontal with respect to a floor surface (or the ground) of a space where the medical observation device 100A is disposed" and a "state where the third axis O3 is substantially horizontal (regarded to be horizontal although not completely horizontal, which will be similarly applied hereinafter) to the floor surface (or the ground) of the space where the medical observation device 100A is disposed".

When the seventh axis O7, which is the active rotation axis, rotates as illustrated in FIG. 5C, for example, the angle a formed between the first axis O1 and the third axis O3 becomes larger than that before the rotation of the seventh axis O7, and as a result, the arm 104A is prevented from being in the predetermined state.

In addition, when the medical observation device 100A rotates the seventh axis O7, which is the active rotation axis, one or more passive rotation axes rotate to absorb the movement of the imaging device 106 caused by the rotational operation of the active rotation axis.

Since the one or more passive rotation axes passively rotate along with the rotational operation of the active rotation axis as described above, a posture of the first axis O1 does not change due to the rotational operation of the active rotation axis. That is, the posture of the imaging device 106 supported by the arm 104A does not change before and after the rotational operation of the active rotation axis in the medical observation device 100A. Thus, even when the medical observation device 100A rotates the seventh axis O7, which is the active rotation axis, the imaging range of the imaging device 106 supported by the arm 104A does not change, and an image of the same portion of the observation target is captured before and after the rotational operation of the active rotation axis. In addition, the possibility that the rotational operation of the active rotation axis interferes with a medical practice of the operator is low since the medical imaging image displayed on the display screen of the display device 200 represents the same portion of the observation target even when the medical observation device 100A rotates the seventh axis O7, which is the active rotation axis.

(B) Second Example of Processing Relating to Control Method

For example, the medical observation device 100A rotates the active rotation axis so as to maintain the posture of the arm 104A. The medical observation device 100A rotates the active rotation axis such that the rotation angle of the second axis O2 maintains a set second range.

The second range according to the present embodiment is a "range in which a user who uses the medical observation device 100A (an example of the medical holding device) easily operates the imaging device 106 (an example of the medical instrument supported by the arm 104A) supported by the arm 104A". The second range is set, for example, in a design stage or the like. An example of the rotation angle of the second axis O2 when the user easily operates the imaging device 106 supported by the arm 104A is 90[°]. Thus, for example, the following example may be described as the second range. Here, E3 and E4 are "0" or a "real number larger than 0" set in a design stage or the like. A value of E3 and a value of E4 may be identical or different. Incidentally, it is a matter of course that the example of the second range is not limited to the following example.

90−$E3$<(Rotation Angle of Second Axis $O2$)<90+$E4$

90−$E3$≤(Rotation Angle of Second Axis $O2$)<90+$E4$

90−$E3$<(Rotation Angle of Second Axis $O2$)≤90+$E4$

90−$E3$≤(Rotation Angle of Second Axis $O2$)≤90+$E4$

Figure 6A:
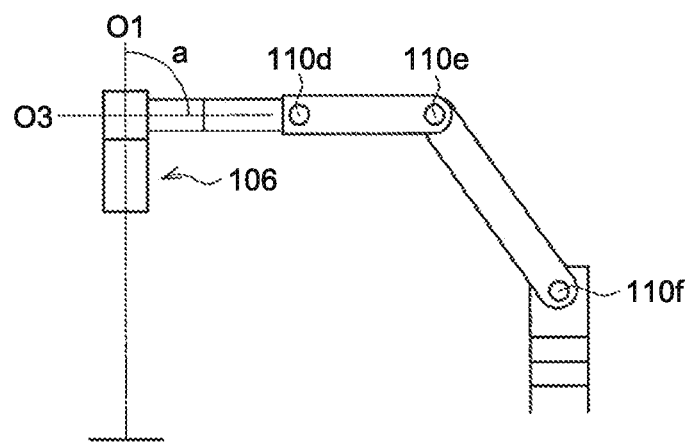
FIGS. 6A to 6C are explanatory views illustrating an example of an operation of an arm according to a second example of the processing relating to the control method of the present embodiment.
Figure 6B:
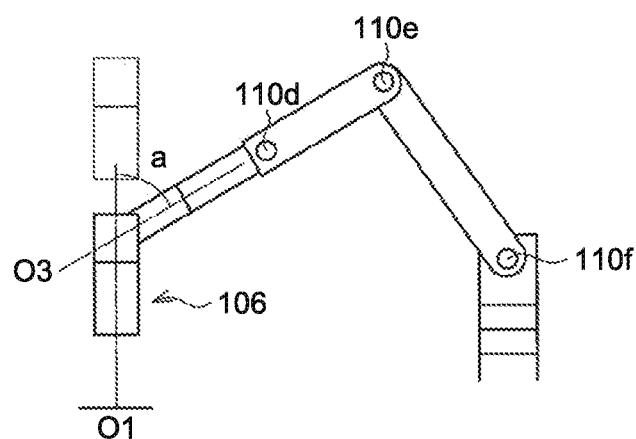
Figure 6C:
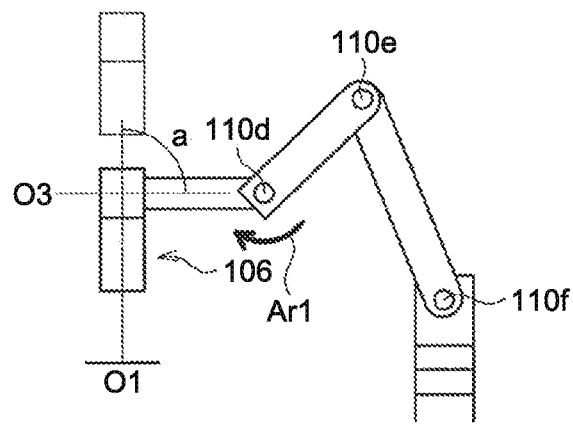

FIGS. 6A to 6C are explanatory views illustrating an example of the operation of the arm 104A according to the second example of the processing relating to the control method of the embodiment. FIGS. 6A to 6C illustrate a part of the arm 104A from the side on which the imaging device 106 is supported to the joint portion 110f corresponding to the fifth axis O5. FIG. 6A illustrates an example of the posture of the arm 104A when it is not determined that the posture approaches the predetermined state. FIG. 6B illustrates an example of the posture of the arm 104A when it is determined that the posture approaches the predetermined state. FIG. 6C illustrates an example of the posture of the arm 104A when the active rotation axis rotates so as to avoid the predetermined state. In FIG. 6A, FIG. 6B, and FIG. 6C, "a" indicates an angle formed between the first axis O1 and the third axis O3. As described above, the angle a formed between the first axis O1 and the third axis O3 corresponds to the rotation angle of the second axis O2 detected by the angle sensor.

When the posture of the arm 104A changes from the posture illustrated in FIG. 6A to the posture illustrated in FIG. 6B, the angle a formed between the first axis O1 and the third axis O3 gradually decreases. The change from the posture illustrated in FIG. 6A to the posture illustrated in FIG. 6B occurs, for example, when an operator tries to bring the imaging device 106 closer to a surgical site as an observation target.

Therefore, when a change in the angle a formed between the first axis O1 and the third axis O3 is detected in the medical observation device 100A, the seventh axis O7, which is the active rotation axis, is rotated as indicated by an arrow Ar1 in FIG. 6C. Specifically, the medical observation device 100A rotates the seventh axis O7 which is the active rotation axis, such that the third axis O3, which is the passive rotation axis, becomes horizontal, which is similar to the process according to the first example.

When the seventh axis O7, which is the active rotation axis, rotates as illustrated in FIG. 6C, for example, the angle a formed between the first axis O1 and the third axis O3 becomes larger than that before the rotation of the seventh axis O7, and as a result, the arm 104A is prevented from being in the predetermined state.

In addition, when the medical observation device 100A rotates the seventh axis O7, which is the active rotation axis, one or more passive rotation axes rotate to absorb the movement of the imaging device 106 caused by the rotational operation of the active rotation axis. Thus, the possibility that the rotational operation of the active rotation axis interferes with a medical practice of the operator is low, which is similar to the case where the process according to the first example is performed.

Furthermore, the posture of the first axis O1 does not change due to the rotational operation of the seventh axis O7 which is the active rotation axis, as illustrated in FIG. 6A and FIG. 6C.

[2-3] Example of Effect Exhibited by Medical Observation Device 100A According to First Embodiment when Control Method According to Present Embodiment is Applied When the control method according to the present embodiment is used, the medical observation device 100A exhibits the following effects, for example. Incidentally, it is a matter of course that the effects exhibited in the medical observation device 100A by using the control method according to the present embodiment are not limited to the following examples.

It is possible to secure the degree of freedom of observation using the imaging device 106 supported by the arm 104A since the angle a formed between the first axis O1 and the third axis O3 does not become a predetermined angle or smaller.

It is possible to maintain the high operability of the arm 104A by controlling the angle a formed between the first axis O1 and the third axis O3 to maintain the predetermined angle.

The actuator configured to cancel a rotational moment generated by the gravity becomes unnecessary with the configuration in which the center of gravity is placed on the rotation axis of each of the first axis O1, the second axis O2, and the third axis O3. Thus, the configuration of the medical observation device 100A can be further simplified as much as the actuator becomes unnecessary.

[3] Medical Observation System According to Second Embodiment

Next, a medical observation system according to a second embodiment will be described. Hereinafter, a difference from the medical observation system 1000 (including the modification) according to the first embodiment will be described, and substantially the same points will not be described.

Figure 7:
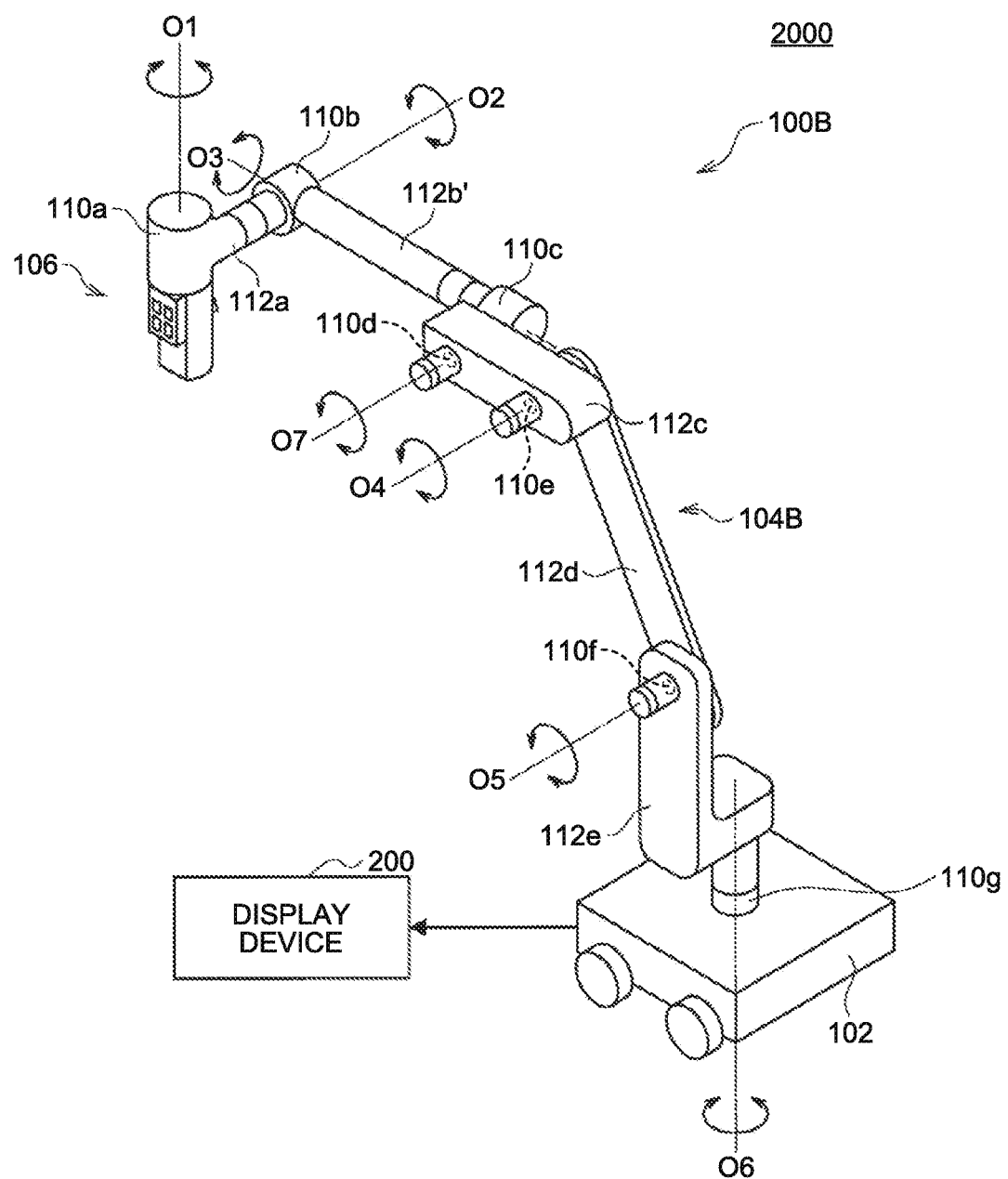
FIG. 7 is an explanatory view illustrating an example of a configuration of a medical observation system according to a second embodiment.

[3-1] Configuration of Medical Observation System According to Second Embodiment FIG. 7 is an explanatory view illustrating an example of a configuration of a medical observation system 2000 according to the second embodiment. The medical observation system 2000 includes, for example, a medical observation device 100B and the display device 200.

A configuration of the medical observation device 100B is different from that of the medical observation device 100A according to the first embodiment illustrated in FIG. 1 in terms of the following points, and the other points are substantially the same.

A torque sensor (not illustrated), an actuator (not illustrated), and an angle sensor (not illustrated) are provided at a joint portion corresponding to each of the first axis O1 to the seventh axis O7 (examples of all passive rotation axes and all active rotation axes). Some or all of the torque sensors provided in the respective joint portions may be torque sensors provided in the medical observation device 100B or may be torque sensors outside the medical observation device 100B. Some or all of the actuators provided in the respective joint portions may be actuators provided in the medical observation device 100B or may be actuators outside the medical observation device 100B. Some or all of the angle sensors provided in the respective joint portions may be angle sensors provided in the medical observation device 100B, or may be angle sensors outside the medical observation device 100B.

A shape of a link 112b' constituting an arm 104B of the medical observation device 100B is different from the shape of the link 112b constituting the arm 104A provided in the medical observation device 100A. Thus, the center of gravity of each link connected to each of the rotation axes is not placed on the rotation axis of each of the first axis O1, the second axis O2, and the third axis O3 in the medical observation device 100B.

The arm 104B of the medical observation device 100B is provided with the angle sensor (not illustrated) that detects a rotation angle of each of the first axis O1 to the seventh axis O7, and thus, it is possible to identify a posture of the arm 104B based on a detection result of each angle sensor. In addition, examples of a case where the posture of the arm 104B is likely to be in the predetermined state include a "case where the first axis O1 is inclined from the vertical direction to the horizontal direction" and a "case where the arm 104B is deformed along with the movement of the first axis O1 so that the link 112b' is inclined from the horizontal direction to the vertical direction" according to the first embodiment described above.

Thus, the medical observation device 100B detects a posture in the case where the posture of the arm 104B is likely to be in the predetermined state, and rotates the seventh axis O7, which is the active rotation axis, so as to prevent the posture of the arm 104B from being in the predetermined state when detecting the posture.

The medical observation device 100B rotates the seventh axis O7, which is the active rotation axis, is rotated such that the third axis O3 becomes horizontal, which is similar to the medical observation device 100A according to the first embodiment, for example. Since the seventh axis O7 is rotated such that the third axis O3 becomes horizontal, the posture of the arm 104B changes such that the link 112b' approaches a horizontal state in the medical observation device 100B. Then, the posture of the arm 104B is maintained in the state where the link 112b' is horizontal (or substantially horizontal) in the medical observation device 100B. In addition, at this time, the posture of the first axis O1 does not change due to the rotational operation of the seventh axis O7 which is the active rotation axis. Incidentally, the medical observation device 100B may maintain the link 112b' in an arbitrary state such that the posture of the arm 104B is prevented from being in the predetermined state without being limited to maintaining the link 112b' to be horizontal (or substantially horizontal).

In addition, when the medical observation device 100B rotates the seventh axis O7, which is the active rotation axis, one or more passive rotation axes rotate to absorb the movement of the imaging device 106 caused by the rotational operation of the active rotation axis, which is similar to the medical observation device 100A according to the first embodiment. Thus, the possibility that the rotational operation of the active rotation axis in the medical observation device 100B interferes with a medical practice of an operator is low.

[3-2] Example of Effect Exhibited by Medical Observation Device According to Second Embodiment when Control Method According to Present Embodiment is Applied When the control method according to the present embodiment is used, the medical observation device 100B exhibits the following effects, for example. Incidentally, it is a matter of course that the effects exhibited in the medical observation device 100B by using the control method according to the present embodiment are not limited to the following examples.

The medical observation device 100B rotates the active rotation axis based on a detection result on the posture of the arm 104B such that the posture of the arm 104B is prevented from being in the predetermined state. Thus, the medical observation device 100B can maintain the posture of the arm 104B in a posture with good operability.

Since the posture of the link 112b' is maintained to be constant by rotating the seventh axis O7, which is the active rotation axis, a user such as the operator does not necessarily concern interference during the operation or vignetting of the field of view by the arm 104B at the time of observing a medical observation image displayed on a display screen of the display device 200.

Since the center of gravity of each link connected to each of the rotation axes is not placed on the rotation axis of each of the first axis O1, the second axis O2, and the third axis O3, the arms 104B can be configured in any shape.

[4] Medical Observation System According to Third Embodiment

Next, a medical observation system according to a third embodiment will be described. Hereinafter, a difference from the medical observation system 1000 (including the modification) according to the first embodiment will be described, and substantially the same points will not be described.

[4-1] Configuration of Medical Observation System According to Third Embodiment

Figure 8:
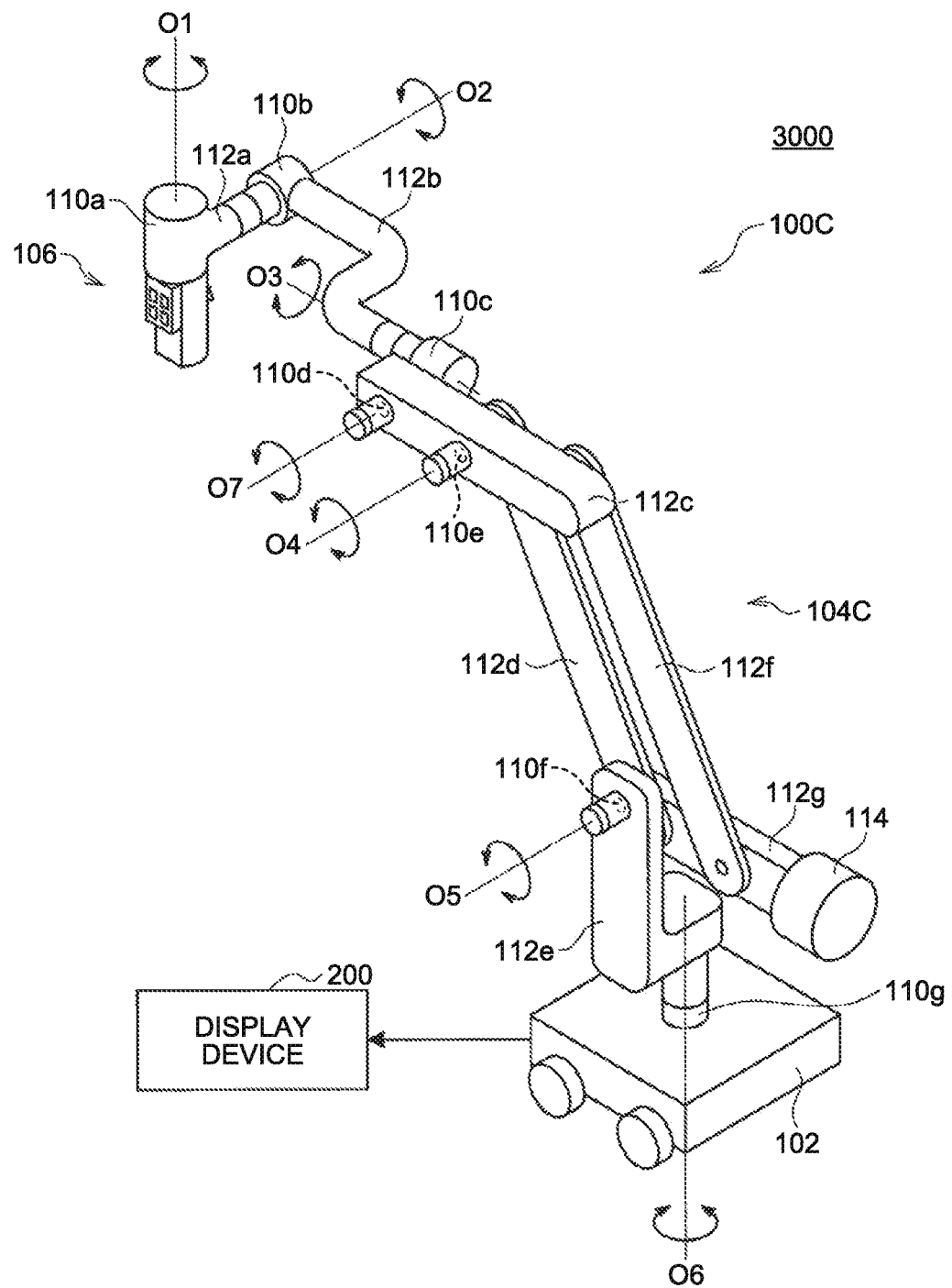
FIG. 8 is an explanatory view illustrating an example of a configuration of a medical observation system according to a third embodiment.

FIG. 8 is an explanatory view illustrating an example of a configuration of a medical observation system 3000 according to the third embodiment. The medical observation system 3000 includes, for example, a medical observation device 100C and the display device 200.

A configuration of the medical observation device 100C is different from that of the medical observation device 100A according to the first embodiment illustrated in FIG. 1 in terms of the following points, and the other points are substantially the same.

An arm 104C further includes a link 112f and a link 112g, and parallel links are formed between the fourth axis O4 and the fifth axis O5 by the link 112c, the link 112d, the link 112f, and the link 112g.

The parallel links are provided with a counterweight 114, and the arm 104C is configured such that the seventh axis O7 is in balance with the fourth axis O4 and the fifth axis O5 at a predetermined angle. That is, the arm 104C provided in the medical observation device 100C includes the counterweight 114 that cancels a rotational moment generated by gravity regarding the degrees of freedom realized by rotational operations of at least one or more passive rotation axes.

As described above, the medical observation device 100C is different from the medical observation device 100A according to the first embodiment in terms of having the configuration in which the arm 104C is provided with the counterweight 114 and in terms that the arm 104C is a balance arm. On the other hand, an operation of the medical observation device 100C realized by applying the control method according to the present embodiment is similar to the operation of the medical observation device 100A according to the first embodiment. That is, the medical observation device 100C rotates the seventh axis O7, which is the active rotation axis, so as to prevent the posture of the arm 104C from being in the predetermined state, which is similar to the medical observation device 100A according to the first embodiment.

[4-2] Example of Effect Exhibited by Medical Observation Device According to Third Embodiment when Control Method According to Present Embodiment is Applied When the control method according to the present embodiment is used, the medical observation device 100C exhibits the following effects, for example. Incidentally, it is a matter of course that the effects exhibited in the medical observation device 100C by using the control method according to the present embodiment are not limited to the following examples.

Since the arm 104C is the balance arm, the amount of unbalance can be suppressed by the counterbalance, and as a result, it is possible to suppress output of an actuator (not illustrated).

Since the arm 104C is the balance arm, for example, the actuators (not illustrated) and torque sensors (not illustrated) provided at joint portions respectively corresponding to the fourth axis O4, the fifth axis O5, and the sixth axis O6 of the arm 104C can be replaced with a brake (not illustrated). Thus, it is possible to reduce the number of actuators and to reduce the control load of the actuators in the medical observation device 100C.

[5] Medical Observation System According to Fourth Embodiment

Next, a medical observation system according to a fourth embodiment will be described. Hereinafter, a difference from the medical observation system 3000 according to the third embodiment will be described, and substantially the same points will not be described.

Figure 9:
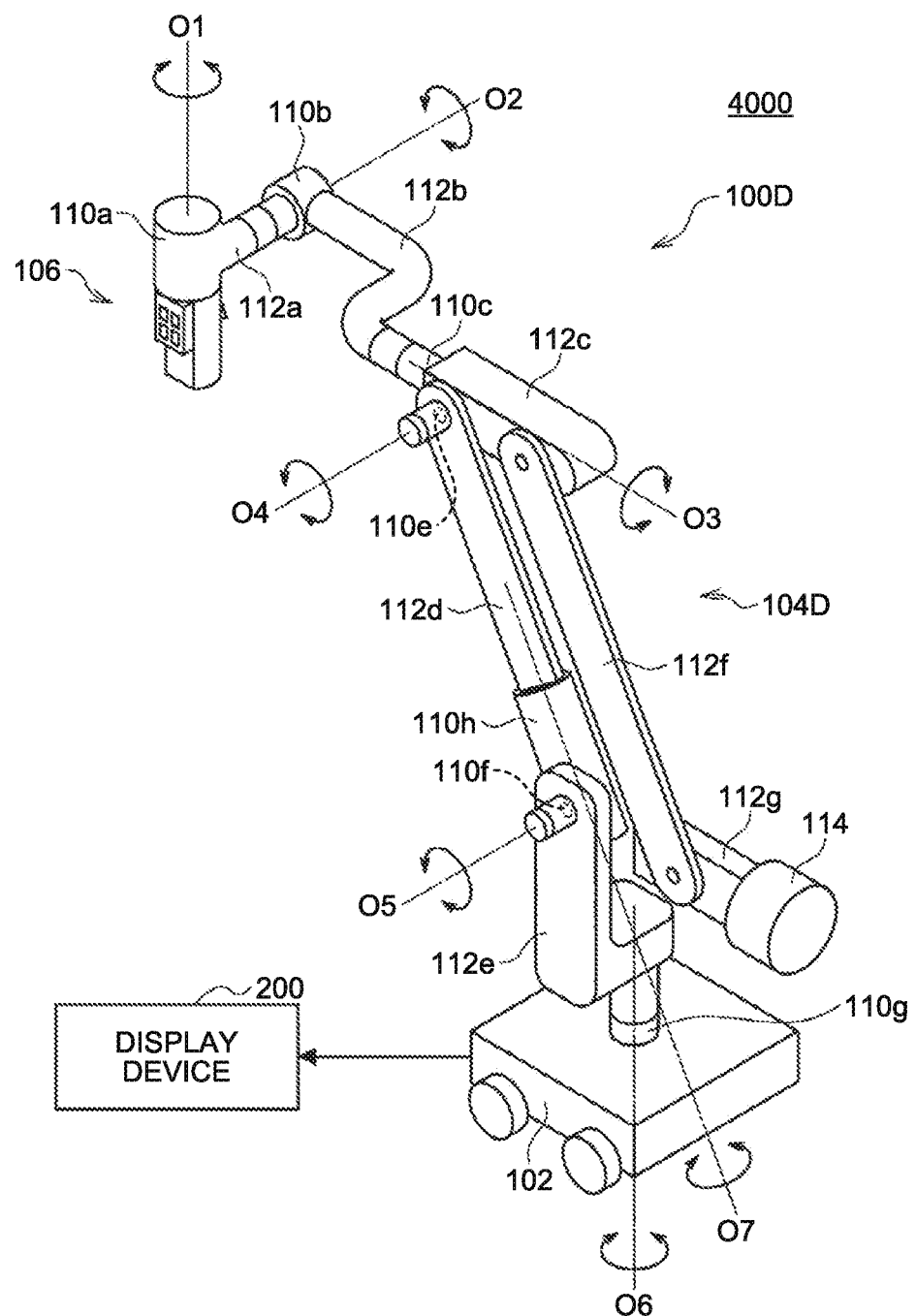
FIG. 9 is an explanatory view illustrating an example of a configuration of a medical observation system according to a fourth embodiment.

[5-1] Configuration of Medical Observation System According to Fourth Embodiment FIG. 9 is an explanatory view illustrating an example of a configuration of a medical observation system 4000 according to the fourth embodiment. The medical observation system 4000 includes, for example, a medical observation device 100D and the display device 200.

A configuration of the medical observation device 100D is different from that of the medical observation device 100C according to the third embodiment illustrated in FIG. 8 in terms of the following points, and the other points are substantially the same.

An arm 104D is different from the arm 104C of the medical observation device 100C according to the third embodiment in terms of a position of the seventh axis O7. Specifically, a joint portion 110h is provided instead of the joint portion 110d, and as a result, the seventh axis O7 is located at the position perpendicular to the fifth axis O5 in the arm 104D. In the arm 104D, the link 112d supported by the fifth axis O5 is rotatably held by the seventh axis O7.

The arm 104D is a balance arm similarly to the arm 104C. However, in the arm 104D, the center of gravity of a structure of the medical observation device 100D held by each of the rotation axes is mounted on the first axis O1 to the seventh axis O7 (examples of all passive rotation axes and all active rotation axes), that is, all the rotation axes. Therefore, in the arm 104D, a shift of the center of gravity does not occur due to the rotation of each axis, and balance is always maintained.

As described above, the medical observation device 100D is different from the medical observation device 100C in terms of the configuration of the balance arm. On the other hand, an operation of the medical observation device 100D realized by applying the control method according to the present embodiment is similar to the operation of the medical observation device 100C according to the third embodiment. That is, the medical observation device 100D rotates the seventh axis O7, which is the active rotation axis, so as to prevent the posture of the arm 104D from being in the predetermined state, which is similar to the medical observation device 100C according to the third embodiment, that is, the medical observation device 100A according to the first embodiment.

In addition, when the arm 104D of the medical observation device 100D is provided with an angle sensor (not illustrated) that detects a rotation angle of each of the first axis O1 to the sixth axis O6, and thus, it is possible to identify a posture of the arm 104D based on a detection result of each angle sensor. Thus, the medical observation device 100D may rotate the active rotation axis so as to prevent the posture of the arm 104D from being in the predetermined state based on a detection result of the posture of the arm 104D, which is similar to the medical observation device 100B according to the second embodiment. When the operation of the arm 104D is controlled similarly to the medical observation device 100B, the posture of the arm 104D is maintained at a predetermined posture, for example, such that the link 112b becomes horizontal (or substantially horizontal).

[5-2] Example of Effect Exhibited by Medical Observation Device According to Fourth Embodiment when Control Method According to Present Embodiment is Applied When the control method according to the present embodiment is used, the medical observation device 100D exhibits the following effects, for example. Incidentally, it is a matter of course that the effects exhibited in the medical observation device 100D by using the control method according to the present embodiment are not limited to the following examples.

Since the arm 104D can achieve perfect balance, it is possible to realize light operability (operability with a small force) even if no actuator is provided at each of the active rotation axes of the arm 104D.

Program According to Present Embodiment

When a program (for example, a program capable of executing the processing relating to the control method according to the present embodiment) configured cause a computer system to function as the medical holding device according to the present embodiment is executed by a processor or the like in the computer system, it is possible to achieve improvement of convenience of a user. Here, a single computer or a plurality of computers can be exemplified as the computer system according to the present embodiment. A series of processes relating to the control method according to the present embodiment are performed by the computer system according to the present embodiment.

In addition, when a program configured to cause a computer system to function as the medical observation device according to the present embodiment (or the control device according to the present embodiment) is executed by a processor or the like in the computer system, it is possible to achieve the effects exhibited in each of the above-described embodiments to which the control method according to the present embodiment is applied.

Although the preferred embodiments of the present disclosure have been described in detail with reference to the accompanying drawings as above, a technical scope of the present disclosure is not limited to such examples. It is apparent that those skilled in the technical field of the present disclosure can conceive various modifications and alterations within a category of the technical idea described in the claims, and it is understood that such modifications and alterations also pertain to the technical scope of the present disclosure.

For example, the case in which the program (computer program) configured to cause the computer system to function as the medical holding device according to the present embodiment is provided has been described as above, but the present embodiment can provide a recording medium storing the above program together.

The above-described configuration is an example of the present embodiment, and pertains to the technical scope of the present disclosure, of course.

In addition, the effects described in the present specification are merely illustrative or exemplary, and are not restrictive. That is, the technique according to the present disclosure can exhibit other effects apparent to those skilled in the art based on the description of the present specification in addition to or instead of the above-described effects.

Incidentally, the following configurations also pertain to the technical scope of the present disclosure.

According to the present disclosure, it is possible to improve the convenience of the user.

Incidentally, the above effects are not necessarily limited, and any of the effects illustrated herein or other effects that may be grasped from the present specification may be exhibited in addition to the above effects or instead of the above effects.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical holding device comprising:
an arm configured by coupling a plurality of links to each other by joints, the arm having at least seven or more degrees of freedom by rotational operations on rotation axes, and being configured to support a medical instrument; and
an arm control circuit configured to control an operation of the arm,
wherein the arm has six degrees of freedom realized by rotational operations of six passive rotation axes that passively rotate and one or more degrees of freedom realized by rotational operations of one or more active rotation axes that actively rotate, and
the arm control circuit is configured to rotate the active rotation axis so as to avoid a predetermined state of a posture of the arm, wherein
a first axis, a second axis, and a third axis, which are a first rotation axis, a second rotation axis, and a third rotation axis, respectively, counted from a side on which the medical instrument is supported are the passive rotation axes, and
the active rotation axis is a fourth or subsequent rotation axis counted from the side on which the medical instrument is supported.

2. The medical holding device according to claim 1, wherein the predetermined state is
a state where the first axis is present on a plane defined by the second axis and the third axis, or
a state where the first axis is present on a plane parallel to the plane defined by the second axis and the third axis.

3. The medical holding device according to claim 1, wherein the predetermined state is a unique state where a number of degrees of freedom decreases, the number of degrees of freedom realized by rotational operations of each of the first axis, the second axis, and the third axis.

4. The medical holding device according to claim 1, wherein a posture of the first axis does not change due to the rotational operation of the active rotation axis.

5. The medical holding device according to claim 1, wherein the arm control circuit is configured to rotate the active rotation axis such that the third axis is horizontal.

6. The medical holding device according to claim 1, wherein the passive rotation axis rotates so as to absorb movement of the medical instrument caused by the rotational operation of the active rotation axis.

7. The medical holding device according to claim 1, wherein the arm control circuit is configured to
determine whether the posture of the arm approaches the predetermined state based on a detection result of an angle sensor configured to detect a rotation angle of the second axis, and
rotate the active rotation axis when determining that the posture of the arm approaches the predetermined state.

8. The medical holding device according to claim 7, wherein the arm control circuit is configured to determine that the posture of the arm approaches the predetermined state when the rotation angle of the second axis detected at a point in time is included in a set first range or when it is estimated that the rotation angle of the second axis to be detected is included in the first range based on the rotation angle of the second axis detected at a point in time and a temporal change of the detected rotation angle of the second axis.

9. The medical holding device according to claim 7, wherein the arm control circuit is configured to rotate the active rotation axis such that the rotation angle of the second axis is not included in the set first range.

10. The medical holding device according to claim 1, wherein the arm control circuit is configured to rotate the active rotation axis such that a rotation angle of the second axis maintains a set second range based on a detection result of an angle sensor that detects the rotation angle of the second axis.

11. The medical holding device according to claim 1, wherein
among the six passive rotation axes, the first axis, the second axis, and the third axis are the passive rotation axes relating to a tilting operation of the medical instrument to be supported, and among the six passive rotation axes, three rotation axes other than the first axis, the second axis, and the third axis are the passive rotation axes defining a three-dimensional position of the medical instrument to be supported.

12. The medical holding device according to claim 1, wherein
a torque sensor configured to detect a torque applied to the passive rotation axis and an actuator controlled by a detection result of the torque sensor are disposed at the joint corresponding to at least one or more of the passive rotation axes, and
the passive rotation axis corresponding to the joint in which the torque sensor and the actuator are disposed passively rotates due to a passive operation of the actuator according to the detection result of the torque sensor.

13. The medical holding device according to claim 12, wherein
the torque sensor is configured to detect a rotational torque generated by gravity and an external force applied to the arm, and
the actuator is configured to operate passively according to the detected external force so as to cancel the detected rotational torque generated by the gravity.

14. The medical holding device according to claim 1, wherein the arm includes a counterweight configured to cancel a rotational moment generated by gravity with respect to the degree of freedom realized by the rotational operation of at least one or more of the passive rotation axes.

15. The medical holding device according to claim 14, wherein a center of gravity of a structure of the medical holding device held by the respective rotation axes is placed on a rotation axis of each of the passive rotation axes and the one or more active rotation axes.

16. The medical holding device according to claim 1, further comprising the medical instrument supported by the arm.

17. A medical observation device comprising:
an imager configured to capture an image of an observation target;
an arm configured by coupling a plurality of links to each other by joints, the arm having at least seven or more degrees of freedom by rotational operations on rotation axes, and being configure to support the imager; and
an arm control circuit configured to control an operation of the arm,
wherein the arm has six degrees of freedom realized by rotational operations of six passive rotation axes that passively rotate and one or more degrees of freedom realized by rotational operations of one or more active rotation axes that actively rotate, and
the arm control circuit is configured to rotate the active rotation axis so as to avoid a predetermined state of a posture of the arm, wherein
a first axis, a second axis, and a third axis, which are a first rotation axis, a second rotation axis, and a third rotation axis, respectively, counted from a side on which the medical instrument is supported are the passive rotation axes, and
the active rotation axis is a fourth or subsequent rotation axis counted from the side on which the medical instrument is supported.

18. A controller of an arm configured by coupling a plurality of links to each other by joints, the arm having at least seven or more degrees of freedom by rotational operations on rotation axes, the at least seven or more degrees of freedom including six degrees of freedom realized by rotational operations of six passive rotation axes that passively rotate and one or more degrees of freedom realized by rotational operations of one or more active rotation axes that actively rotate being, the arm being configured to support a medical instrument, wherein a first axis, a second axis, and a third axis, which are a first rotation axis, a second rotation axis, and a third rotation axis, respectively, counted from a side on which the medical instrument is supported are the passive rotation axes, and the active rotation axis is a fourth or subsequent rotation axis counted from the side on which the medical instrument is supported, the controller comprising
an arm control circuit configured to:
determine whether a posture of the arm approaches a predetermined state based on a detection result of an angle sensor configured to detect a rotation angle of the second axis, and
on condition that the posture of the arm approaches the predetermined state, control the arm to rotate the active rotation axis.

19. The controller to claim 18, wherein the arm control circuit is configured to determine that the posture of the arm approaches the predetermined state when the rotation angle of the second axis detected at a point in time is included in a set first range or when it is estimated that the rotation angle of the second axis to be detected is included in the first range based on the rotation angle of the second axis detected at a point in time and a temporal change of the detected rotation angle of the second axis.

20. The controller to claim 18, wherein the arm control circuit is configured to rotate the active rotation axis such that the third axis is horizontal.

\* \* \* \* \*